US011992339B2

(12) United States Patent
Kirkup et al.

(10) Patent No.: US 11,992,339 B2
(45) Date of Patent: May 28, 2024

(54) SYSTEMS AND METHODS FOR DYNAMIC NEUROPHYSIOLOGICAL STIMULATION

(71) Applicant: Cadwell Laboratories, Inc., Kennewick, WA (US)

(72) Inventors: Melissa Kirkup, West Linn, OR (US); Richard A. Villarreal, West Richland, WA (US); John A. Cadwell, Jr., Richland, WA (US)

(*) Notice: Subject to any disclaimer, the term of this patent is extended or adjusted under 35 U.S.C. 154(b) by 790 days.

(21) Appl. No.: 16/402,544

(22) Filed: May 3, 2019

(65) Prior Publication Data
US 2019/0336073 A1 Nov. 7, 2019

Related U.S. Application Data

(60) Provisional application No. 62/666,959, filed on May 4, 2018.

(51) Int. Cl.
*A61B 5/00* (2006.01)
*A61B 5/24* (2021.01)
*A61B 5/296* (2021.01)
*A61B 5/389* (2021.01)
*A61B 18/12* (2006.01)

(52) U.S. Cl.
CPC .............. *A61B 5/4893* (2013.01); *A61B 5/24* (2021.01); *A61B 5/296* (2021.01); *A61B 5/389* (2021.01); *A61B 5/4064* (2013.01); *A61B 2018/1253* (2013.01); *A61B 2018/126* (2013.01)

(58) Field of Classification Search
CPC ......... A61B 5/4893; A61B 5/24; A61B 5/296; A61B 5/389; A61B 5/4064; A61B 2018/1253; A61B 2018/126; A61B 2018/00839; A61B 2018/167
See application file for complete search history.

(56) References Cited

U.S. PATENT DOCUMENTS

| 751,475 A | 2/1904 | De Vilbiss |
| 972,983 A | 10/1910 | Arthur |
| 1,328,624 A | 1/1920 | Graham |

(Continued)

FOREIGN PATENT DOCUMENTS

| AU | 607977 B2 | 3/1991 |
| AU | 2005269287 A1 | 2/2006 |

(Continued)

OTHER PUBLICATIONS

Review of section 510(k) premarket notification for "K013215: NuVasive NeuroVision JJB System", Department of Health and Human Services, FDA, Oct. 16, 2001.

(Continued)

*Primary Examiner* — David J. McCrosky
(74) *Attorney, Agent, or Firm* — Novel IP

(57) ABSTRACT

An intraoperative neurophysiological monitoring (IONM) system for identifying and assessing neural structures comprises at least one probe, at least one reference electrode, at least one strip or grid electrode, at least one sensing electrode, and a stimulation module. Threshold responses determined by stimulation during a surgical procedure are used to identify and assess functionality of neural structures. The identified neural structures are avoided and preserved while diseased or damaged tissue is resected during said surgical procedure.

23 Claims, 11 Drawing Sheets

(56) References Cited

U.S. PATENT DOCUMENTS

| | | |
|---|---|---|
| 1,477,527 A | 12/1923 | Raettig |
| 1,548,184 A | 8/1925 | Cameron |
| 1,717,480 A | 6/1929 | Wappler |
| 1,842,323 A | 1/1932 | Lorand |
| 2,110,735 A | 3/1938 | Marton |
| 2,320,709 A | 6/1943 | Arnesen |
| 2,516,882 A | 8/1950 | Kalom |
| 2,704,064 A | 3/1955 | Fizzell |
| 2,736,002 A | 2/1956 | Oriel |
| 2,807,259 A | 9/1957 | Guerriero |
| 2,808,826 A | 10/1957 | Reiner |
| 2,994,324 A | 8/1961 | Lemos |
| 3,035,580 A | 5/1962 | Guiorguiev |
| 3,057,356 A | 10/1962 | Greatbatch |
| 3,060,923 A | 10/1962 | Reiner |
| 3,087,486 A | 4/1963 | Kilpatrick |
| 3,147,750 A | 9/1964 | Fry |
| 3,188,605 A | 6/1965 | Slenker |
| 3,212,496 A | 10/1965 | Preston |
| 3,219,029 A | 11/1965 | Richards |
| 3,313,293 A | 4/1967 | Chesebrough |
| 3,364,929 A | 1/1968 | Ide |
| 3,580,242 A | 5/1971 | La Croix |
| 3,611,262 A | 10/1971 | Marley |
| 3,617,616 A | 11/1971 | O'Loughlin |
| 3,641,993 A | 2/1972 | Gaarder |
| 3,646,500 A | 2/1972 | Wessely |
| 3,651,812 A | 3/1972 | Samuels |
| 3,662,744 A | 5/1972 | Richardson |
| 3,664,329 A | 5/1972 | Naylor |
| 3,682,162 A | 8/1972 | Colyer |
| 3,703,900 A | 11/1972 | Holznagel |
| 3,718,132 A | 2/1973 | Holt |
| 3,733,574 A | 5/1973 | Scoville |
| 3,785,368 A | 1/1974 | McCarthy |
| 3,830,226 A | 8/1974 | Staub |
| 3,857,398 A | 12/1974 | Rubin |
| 3,880,144 A | 4/1975 | Coursin |
| 3,933,157 A | 1/1976 | Bjurwill |
| 3,957,036 A | 5/1976 | Normann |
| 3,960,141 A | 6/1976 | Bolduc |
| 3,985,125 A | 10/1976 | Rose |
| 4,062,365 A | 12/1977 | Kameny |
| 4,088,141 A | 5/1978 | Niemi |
| 4,099,519 A | 7/1978 | Warren |
| 4,127,312 A | 11/1978 | Fleischhacker |
| 4,141,365 A | 2/1979 | Fischell |
| 4,155,353 A | 5/1979 | Rea |
| 4,164,214 A | 8/1979 | Pelzner |
| 4,175,551 A | 11/1979 | D Haenens |
| 4,177,799 A | 12/1979 | Masreliez |
| 4,184,492 A | 1/1980 | Fastenmeier |
| 4,200,104 A | 4/1980 | Harris |
| 4,204,545 A | 5/1980 | Yamakoshi |
| 4,207,897 A | 6/1980 | Evatt |
| 4,224,949 A | 9/1980 | Scott |
| 4,226,228 A | 10/1980 | Shin |
| 4,232,680 A | 11/1980 | Hudleson |
| 4,233,987 A | 11/1980 | Feingold |
| 4,235,242 A | 11/1980 | Heule |
| 4,263,899 A | 4/1981 | Burgin |
| 4,265,237 A | 5/1981 | Schwanbom |
| 4,285,347 A | 8/1981 | Hess |
| 4,291,705 A | 9/1981 | Severinghaus |
| 4,294,245 A | 10/1981 | Bussey |
| 4,295,703 A | 10/1981 | Osborne |
| 4,299,230 A | 11/1981 | Kubota |
| 4,308,012 A | 12/1981 | Tamler |
| 4,331,157 A | 5/1982 | Keller, Jr. |
| 4,372,319 A | 2/1983 | Ichinomiya |
| 4,373,531 A | 2/1983 | Wittkampf |
| 4,374,517 A | 2/1983 | Hagiwara |
| 4,402,323 A | 9/1983 | White |
| 4,444,187 A | 4/1984 | Perlin |
| 4,461,300 A | 7/1984 | Christensen |
| 4,469,098 A | 9/1984 | Davi |
| 4,483,338 A | 11/1984 | Bloom |
| 4,485,823 A | 12/1984 | Yamaguchi |
| 4,487,489 A | 12/1984 | Takamatsu |
| 4,503,842 A | 3/1985 | Takayama |
| 4,503,863 A | 3/1985 | Katims |
| 4,510,939 A | 4/1985 | Brenman |
| 4,515,168 A | 5/1985 | Chester |
| 4,517,976 A | 5/1985 | Murakoshi |
| 4,517,983 A | 5/1985 | Toyosu |
| 4,519,403 A | 5/1985 | Dickhudt |
| 4,537,198 A | 8/1985 | Corbett |
| 4,545,374 A | 10/1985 | Jacobson |
| 4,557,273 A | 12/1985 | Stoller |
| 4,558,703 A | 12/1985 | Mark |
| 4,561,445 A | 12/1985 | Berke |
| 4,562,832 A | 1/1986 | Wilder |
| 4,565,200 A | 1/1986 | Cosman |
| 4,570,640 A | 2/1986 | Barsa |
| 4,573,448 A | 3/1986 | Kambin |
| 4,573,449 A | 3/1986 | Warnke |
| 4,576,178 A | 3/1986 | Johnson |
| 4,582,063 A | 4/1986 | Mickiewicz |
| 4,592,369 A | 6/1986 | Davis |
| 4,595,018 A | 6/1986 | Rantala |
| 4,616,635 A | 10/1986 | Caspar |
| 4,616,660 A | 10/1986 | Johns |
| 4,622,973 A | 11/1986 | Agarwala |
| 4,633,889 A | 1/1987 | Talalla |
| 4,641,661 A | 2/1987 | Kalarickal |
| 4,643,507 A | 2/1987 | Coldren |
| 4,658,835 A | 4/1987 | Pohndorf |
| 4,667,676 A | 5/1987 | Guinta |
| 4,697,598 A | 10/1987 | Bernard |
| 4,697,599 A | 10/1987 | Woodley |
| 4,705,049 A | 11/1987 | John |
| 4,716,901 A | 1/1988 | Jackson |
| 4,739,772 A | 4/1988 | Hokanson |
| 4,744,371 A | 5/1988 | Harris |
| 4,759,377 A | 7/1988 | Dykstra |
| 4,763,666 A | 8/1988 | Strian |
| 4,765,311 A | 8/1988 | Kulik |
| 4,784,150 A | 11/1988 | Voorhies |
| 4,785,812 A | 11/1988 | Pihl |
| 4,795,998 A | 1/1989 | Dunbar |
| 4,807,642 A | 2/1989 | Brown |
| 4,807,643 A | 2/1989 | Rosier |
| 4,817,587 A | 4/1989 | Janese |
| 4,817,628 A | 4/1989 | Zealear |
| 4,827,935 A | 5/1989 | Geddes |
| 4,841,973 A | 6/1989 | Stecker |
| 4,844,091 A | 7/1989 | Bellak |
| 4,862,891 A | 9/1989 | Smith |
| 4,892,105 A | 1/1990 | Prass |
| 4,895,152 A | 1/1990 | Callaghan |
| 4,920,968 A | 5/1990 | Takase |
| 4,926,865 A | 5/1990 | Oman |
| 4,926,880 A | 5/1990 | Claude |
| 4,934,377 A | 6/1990 | Bova |
| 4,934,378 A | 6/1990 | Perry, Jr. |
| 4,934,957 A | 6/1990 | Bellusci |
| 4,962,766 A | 10/1990 | Herzon |
| 4,964,411 A | 10/1990 | Johnson |
| 4,964,811 A | 10/1990 | Hayes, Sr. |
| 4,984,578 A | 1/1991 | Keppel |
| 4,998,796 A | 3/1991 | Bonanni |
| 5,007,902 A | 4/1991 | Witt |
| 5,015,247 A | 5/1991 | Michelson |
| 5,018,526 A | 5/1991 | Gaston-Johansson |
| 5,020,542 A | 6/1991 | Rossmann |
| 5,024,228 A | 6/1991 | Goldstone |
| 5,058,602 A | 10/1991 | Brody |
| 5,080,606 A | 1/1992 | Burkard |
| 5,081,990 A | 1/1992 | Deletis |
| 5,085,226 A | 2/1992 | Deluca |
| 5,092,344 A | 3/1992 | Lee |
| 5,095,905 A | 3/1992 | Klepinski |
| 5,125,406 A | 6/1992 | Goldstone |
| 5,127,403 A | 7/1992 | Brownlee |

(56) References Cited

U.S. PATENT DOCUMENTS

| | | |
|---|---|---|
| 5,131,389 A | 7/1992 | Giordani |
| 5,143,081 A | 9/1992 | Young |
| 5,146,920 A | 9/1992 | Yuuchi |
| 5,161,533 A | 11/1992 | Prass |
| 5,163,328 A | 11/1992 | Holland |
| 5,171,279 A | 12/1992 | Mathews |
| 5,190,048 A | 3/1993 | Wilkinson |
| 5,191,896 A | 3/1993 | Gafni |
| 5,195,530 A | 3/1993 | Shindel |
| 5,195,532 A | 3/1993 | Schumacher |
| 5,196,015 A | 3/1993 | Neubardt |
| 5,199,899 A | 4/1993 | Ittah |
| 5,201,325 A | 4/1993 | McEwen |
| 5,215,100 A | 6/1993 | Spitz |
| RE34,390 E | 9/1993 | Culver |
| 5,253,656 A | 10/1993 | Rincoe |
| 5,255,691 A | 10/1993 | Otten |
| 5,277,197 A | 1/1994 | Church |
| 5,282,468 A | 2/1994 | Klepinski |
| 5,284,153 A | 2/1994 | Raymond |
| 5,284,154 A | 2/1994 | Raymond |
| 5,292,309 A | 3/1994 | Van Tassel |
| 5,299,563 A | 4/1994 | Seton |
| 5,306,236 A | 4/1994 | Blumenfeld |
| 5,312,417 A | 5/1994 | Wilk |
| 5,313,956 A | 5/1994 | Knutsson |
| 5,313,962 A | 5/1994 | Obenchain |
| 5,327,902 A | 7/1994 | Lemmen |
| 5,333,618 A | 8/1994 | Lekhtman |
| 5,343,871 A | 9/1994 | Bittman |
| 5,347,989 A | 9/1994 | Monroe |
| 5,358,423 A | 10/1994 | Burkhard |
| 5,358,514 A | 10/1994 | Schulman |
| 5,368,043 A | 11/1994 | Sunouchi |
| 5,373,317 A | 12/1994 | Salvati |
| 5,375,067 A | 12/1994 | Berchin |
| 5,377,667 A | 1/1995 | Patton |
| 5,381,805 A | 1/1995 | Tuckett |
| 5,383,876 A | 1/1995 | Nardella |
| 5,389,069 A | 2/1995 | Weaver |
| 5,405,365 A | 4/1995 | Hoegnelid |
| 5,413,111 A | 5/1995 | Wilkinson |
| 5,454,365 A | 10/1995 | Bonutti |
| 5,470,349 A | 11/1995 | Kleditsch |
| 5,472,426 A | 12/1995 | Bonati |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,485,852 A | 1/1996 | Johnson |
| 5,491,299 A | 2/1996 | Naylor |
| 5,514,005 A | 5/1996 | Jaycox |
| 5,514,165 A | 5/1996 | Malaugh |
| 5,522,386 A | 6/1996 | Lerner |
| 5,540,235 A | 7/1996 | Wilson |
| 5,549,656 A | 8/1996 | Reiss |
| 5,560,372 A | 10/1996 | Cory |
| 5,565,779 A | 10/1996 | Arakawa |
| 5,566,678 A | 10/1996 | Cadwell |
| 5,569,248 A | 10/1996 | Mathews |
| 5,575,284 A | 11/1996 | Athan |
| 5,579,781 A | 12/1996 | Cooke |
| 5,591,216 A | 1/1997 | Testerman |
| 5,593,429 A | 1/1997 | Ruff |
| 5,599,279 A | 2/1997 | Slotman |
| 5,601,608 A | 2/1997 | Mouchawar |
| 5,618,208 A | 4/1997 | Crouse |
| 5,620,483 A | 4/1997 | Minogue |
| 5,622,515 A | 4/1997 | Hotea |
| 5,630,813 A | 5/1997 | Kieturakis |
| 5,634,472 A | 6/1997 | Raghuprasad |
| 5,671,752 A | 9/1997 | Sinderby |
| 5,681,265 A | 10/1997 | Maeda |
| 5,687,080 A | 11/1997 | Hoyt |
| 5,707,359 A | 1/1998 | Bufalini |
| 5,711,307 A | 1/1998 | Smits |
| 5,725,514 A | 3/1998 | Grinblat |
| 5,728,046 A | 3/1998 | Mayer |
| 5,741,253 A | 4/1998 | Michelson |
| 5,741,261 A | 4/1998 | Moskovitz |
| 5,759,159 A | 6/1998 | Masreliez |
| 5,769,781 A | 6/1998 | Chappuis |
| 5,772,597 A | 6/1998 | Goldberger |
| 5,772,661 A | 6/1998 | Michelson |
| 5,775,331 A | 7/1998 | Raymond |
| 5,776,144 A | 7/1998 | Leysieffer |
| 5,779,642 A | 7/1998 | Nightengale |
| 5,785,648 A | 7/1998 | Min |
| 5,785,658 A | 7/1998 | Benaron |
| 5,792,044 A | 8/1998 | Foley |
| 5,795,291 A | 8/1998 | Koros |
| 5,797,854 A | 8/1998 | Hedgecock |
| 5,806,522 A | 9/1998 | Katims |
| 5,814,073 A | 9/1998 | Bonutti |
| 5,830,150 A | 11/1998 | Palmer |
| 5,830,151 A | 11/1998 | Hadzic |
| 5,833,714 A | 11/1998 | Loeb |
| 5,836,880 A | 11/1998 | Pratt |
| 5,851,191 A | 12/1998 | Gozani |
| 5,853,373 A | 12/1998 | Griffith |
| 5,857,986 A | 1/1999 | Moriyasu |
| 5,860,829 A | 1/1999 | Hower |
| 5,860,973 A | 1/1999 | Michelson |
| 5,862,314 A | 1/1999 | Jeddeloh |
| 5,868,668 A | 2/1999 | Weiss |
| 5,872,314 A | 2/1999 | Clinton |
| 5,885,210 A | 3/1999 | Cox |
| 5,885,219 A | 3/1999 | Nightengale |
| 5,888,196 A | 3/1999 | Bonutti |
| 5,891,147 A | 4/1999 | Moskovitz |
| 5,895,298 A | 4/1999 | Faupel |
| 5,902,231 A | 5/1999 | Foley |
| 5,924,984 A | 7/1999 | Rao |
| 5,928,030 A | 7/1999 | Daoud |
| 5,928,139 A | 7/1999 | Koros |
| 5,928,158 A | 7/1999 | Aristides |
| 5,931,777 A | 8/1999 | Sava |
| 5,944,658 A | 8/1999 | Koros |
| 5,954,635 A | 9/1999 | Foley |
| 5,954,716 A | 9/1999 | Sharkey |
| 5,993,385 A | 11/1999 | Johnston |
| 5,993,434 A | 11/1999 | Dev |
| 6,004,262 A | 12/1999 | Putz |
| 6,004,312 A | 12/1999 | Finneran |
| 6,004,341 A | 12/1999 | Zhu |
| 6,009,347 A | 12/1999 | Hofmann |
| 6,011,985 A | 1/2000 | Athan |
| 6,027,456 A | 2/2000 | Feler |
| 6,029,090 A | 2/2000 | Herbst |
| 6,038,469 A | 3/2000 | Karlsson |
| 6,038,477 A | 3/2000 | Kayyali |
| 6,042,540 A | 3/2000 | Johnston |
| 6,050,992 A | 4/2000 | Nichols |
| 6,074,343 A | 6/2000 | Nathanson |
| 6,077,237 A | 6/2000 | Campbell |
| 6,095,987 A | 8/2000 | Shmulewitz |
| 6,104,957 A | 8/2000 | Alo |
| 6,104,960 A | 8/2000 | Duysens |
| 6,119,068 A | 9/2000 | Kannonji |
| 6,120,503 A | 9/2000 | Michelson |
| 6,126,660 A | 10/2000 | Dietz |
| 6,128,576 A | 10/2000 | Nishimoto |
| 6,132,386 A | 10/2000 | Gozani |
| 6,132,387 A | 10/2000 | Gozani |
| 6,135,965 A | 10/2000 | Tumer |
| 6,139,493 A | 10/2000 | Koros |
| 6,139,545 A | 10/2000 | Utley |
| 6,146,334 A | 11/2000 | Laserow |
| 6,146,335 A | 11/2000 | Gozani |
| 6,152,871 A | 11/2000 | Foley |
| 6,161,047 A | 12/2000 | King |
| 6,181,961 B1 | 1/2001 | Prass |
| 6,196,969 B1 | 3/2001 | Bester |
| 6,206,826 B1 | 3/2001 | Mathews |

(56) References Cited

U.S. PATENT DOCUMENTS

| | | |
|---|---|---|
| 6,210,324 B1 | 4/2001 | Reno |
| 6,214,035 B1 | 4/2001 | Streeter |
| 6,224,545 B1 | 5/2001 | Cocchia |
| 6,224,549 B1 | 5/2001 | Drongelen |
| 6,234,953 B1 | 5/2001 | Thomas |
| 6,249,706 B1 | 6/2001 | Sobota |
| 6,259,945 B1 | 7/2001 | Epstein |
| 6,266,558 B1 | 7/2001 | Gozani |
| 6,273,905 B1 | 8/2001 | Streeter |
| 6,287,322 B1 | 9/2001 | Zhu |
| 6,292,701 B1 | 9/2001 | Prass |
| 6,298,256 B1 | 10/2001 | Meyer |
| 6,302,842 B1 | 10/2001 | Auerbach |
| 6,306,100 B1 | 10/2001 | Prass |
| 6,309,349 B1 | 10/2001 | Bertolero |
| 6,312,392 B1 | 11/2001 | Herzon |
| 6,314,324 B1 | 11/2001 | Lattner |
| 6,325,764 B1 | 12/2001 | Griffith |
| 6,334,068 B1 | 12/2001 | Hacker |
| 6,346,078 B1 | 2/2002 | Ellman |
| 6,348,058 B1 | 2/2002 | Melkent |
| 6,366,813 B1 | 4/2002 | DiLorenzo |
| 6,391,005 B1 | 5/2002 | Lum |
| 6,393,325 B1 | 5/2002 | Mann |
| 6,425,859 B1 | 7/2002 | Foley |
| 6,425,901 B1 | 7/2002 | Zhu |
| 6,441,747 B1 | 8/2002 | Khair |
| 6,450,952 B1 | 9/2002 | Rioux |
| 6,451,015 B1 | 9/2002 | Rittman, III |
| 6,461,352 B2 | 10/2002 | Morgan |
| 6,466,817 B1 | 10/2002 | Kaula |
| 6,487,446 B1 | 11/2002 | Hill |
| 6,500,128 B2 | 12/2002 | Marino |
| 6,500,173 B2 | 12/2002 | Underwood |
| 6,500,180 B1 | 12/2002 | Foley |
| 6,500,210 B1 | 12/2002 | Sabolich |
| 6,507,755 B1 | 1/2003 | Gozani |
| 6,511,427 B1 | 1/2003 | Sliwa, Jr. |
| 6,535,759 B1 | 3/2003 | Epstein |
| 6,543,299 B2 | 4/2003 | Taylor |
| 6,546,271 B1 | 4/2003 | Reisfeld |
| 6,564,078 B1 | 5/2003 | Marino |
| 6,568,961 B1 | 5/2003 | Liburdi |
| 6,572,545 B2 | 6/2003 | Knobbe |
| 6,577,236 B2 | 6/2003 | Harman |
| 6,579,244 B2 | 6/2003 | Goodwin |
| 6,582,441 B1 | 6/2003 | He |
| 6,585,638 B1 | 7/2003 | Yamamoto |
| 6,609,018 B2 | 8/2003 | Cory |
| 6,618,626 B2 | 9/2003 | West, Jr. |
| 6,623,500 B1 | 9/2003 | Cook |
| 6,638,101 B1 | 10/2003 | Botelho |
| 6,692,258 B1 | 2/2004 | Kurzweil |
| 6,712,795 B1 | 3/2004 | Cohen |
| 6,719,692 B2 | 4/2004 | Kleffner |
| 6,730,021 B2 | 5/2004 | Vassiliades, Jr. |
| 6,770,074 B2 | 8/2004 | Michelson |
| 6,805,668 B1 | 10/2004 | Cadwell |
| 6,819,956 B2 | 11/2004 | DiLorenzo |
| 6,839,594 B2 | 1/2005 | Cohen |
| 6,847,849 B2 | 1/2005 | Mamo |
| 6,851,430 B2 | 2/2005 | Tsou |
| 6,855,105 B2 | 2/2005 | Jackson, III |
| 6,870,109 B1 | 3/2005 | Villarreal |
| 6,901,928 B2 | 6/2005 | Loubser |
| 6,902,569 B2 | 6/2005 | Parmer |
| 6,916,294 B2 | 7/2005 | Ayad |
| 6,916,330 B2 | 7/2005 | Simonson |
| 6,926,728 B2 | 8/2005 | Zucherman |
| 6,929,606 B2 | 8/2005 | Ritland |
| 6,932,816 B2 | 8/2005 | Phan |
| 6,945,933 B2 | 9/2005 | Branch |
| 7,024,247 B2 | 4/2006 | Gliner |
| 7,072,521 B1 | 7/2006 | Cadwell |
| 7,079,883 B2 | 7/2006 | Marino |
| 7,089,059 B1 | 8/2006 | Pless |
| 7,104,965 B1 | 9/2006 | Jiang |
| 7,129,836 B2 | 10/2006 | Lawson |
| 7,153,279 B2 | 12/2006 | Ayad |
| 7,156,686 B1 | 1/2007 | Sekela |
| 7,177,677 B2 | 2/2007 | Kaula |
| 7,214,197 B2 | 5/2007 | Prass |
| 7,216,001 B2 * | 5/2007 | Hacker ............... A61B 5/4041 607/63 |
| 7,230,688 B1 | 6/2007 | Villarreal |
| 7,236,822 B2 | 6/2007 | Dobak, III |
| 7,258,688 B1 | 8/2007 | Shah |
| 7,261,688 B2 | 8/2007 | Smith |
| 7,294,127 B2 | 11/2007 | Leung |
| 7,306,563 B2 | 12/2007 | Huang |
| 7,310,546 B2 | 12/2007 | Prass |
| 7,353,068 B2 * | 4/2008 | Tanaka ............... A61B 18/14 700/83 |
| 7,363,079 B1 | 4/2008 | Thacker |
| 7,374,448 B2 | 5/2008 | Jepsen |
| D574,955 S | 8/2008 | Lash |
| 7,470,236 B1 | 12/2008 | Kelleher |
| 7,496,407 B2 | 2/2009 | Odderson |
| 7,522,953 B2 | 4/2009 | Kaula |
| 7,546,993 B1 | 6/2009 | Walker |
| 7,605,738 B2 | 10/2009 | Kuramochi |
| 7,664,544 B2 | 2/2010 | Miles |
| 7,689,292 B2 | 3/2010 | Hadzic |
| 7,713,210 B2 | 5/2010 | Byrd |
| D621,041 S | 8/2010 | Mao |
| 7,775,974 B2 | 8/2010 | Buckner |
| 7,789,695 B2 | 9/2010 | Radle |
| 7,789,833 B2 | 9/2010 | Urbano |
| 7,801,601 B2 | 9/2010 | Maschino |
| 7,824,410 B2 | 11/2010 | Simonson |
| 7,869,881 B2 | 1/2011 | Libbus |
| 7,878,981 B2 | 2/2011 | Strother |
| 7,914,350 B1 | 3/2011 | Bozich |
| 7,963,927 B2 | 6/2011 | Kelleher |
| 7,974,702 B1 | 7/2011 | Fain |
| 7,983,761 B2 | 7/2011 | Giuntoli |
| 7,987,001 B2 | 7/2011 | Teichman |
| 7,988,688 B2 | 8/2011 | Webb |
| 7,993,269 B2 | 8/2011 | Donofrio |
| 8,002,770 B2 | 8/2011 | Swanson |
| 8,061,014 B2 | 11/2011 | Smith |
| 8,068,910 B2 | 11/2011 | Gerber |
| 8,126,736 B2 | 2/2012 | Anderson |
| 8,137,284 B2 | 3/2012 | Miles |
| 8,147,421 B2 | 4/2012 | Farquhar |
| 8,160,694 B2 | 4/2012 | Salmon |
| 8,192,437 B2 | 6/2012 | Simonson |
| 8,255,045 B2 * | 8/2012 | Gharib ............... A61B 5/24 600/547 |
| 8,295,933 B2 | 10/2012 | Gerber |
| D670,656 S | 11/2012 | Jepsen |
| 8,311,791 B1 | 11/2012 | Avisar |
| 8,323,208 B2 | 12/2012 | Davis |
| 8,343,079 B2 | 1/2013 | Bartol |
| 8,374,673 B2 | 2/2013 | Adcox |
| RE44,049 E | 3/2013 | Herzon |
| 8,419,758 B2 | 4/2013 | Smith |
| 8,428,733 B2 | 4/2013 | Carlson |
| 8,457,734 B2 | 6/2013 | Libbus |
| 8,498,717 B2 | 7/2013 | Lee |
| 8,515,520 B2 | 8/2013 | Brunnett |
| 8,568,312 B2 | 10/2013 | Cusimano Reaston |
| 8,568,317 B1 | 10/2013 | Gharib |
| 8,594,779 B2 | 11/2013 | Denison |
| 8,647,124 B2 | 2/2014 | Bardsley |
| 8,670,830 B2 | 3/2014 | Carlson |
| 8,680,986 B2 | 3/2014 | Costantino |
| 8,688,237 B2 | 4/2014 | Stanislaus |
| 8,695,957 B2 | 4/2014 | Quintania |
| 8,740,783 B2 | 6/2014 | Gharib |
| 8,753,333 B2 | 6/2014 | Johnson |
| 8,764,654 B2 | 7/2014 | Chmiel |
| 8,805,527 B2 | 8/2014 | Mumford |
| 8,876,813 B2 | 11/2014 | Min |

(56) References Cited

U.S. PATENT DOCUMENTS

| | | |
|---|---|---|
| 8,886,280 B2 | 11/2014 | Kartush |
| 8,892,259 B2 | 11/2014 | Bartol |
| 8,926,509 B2 | 1/2015 | Magar |
| 8,942,797 B2 | 1/2015 | Bartol |
| 8,956,418 B2 | 2/2015 | Wasielewski |
| 8,958,869 B2 | 2/2015 | Kelleher |
| 8,971,983 B2 | 3/2015 | Gilmore |
| 8,986,301 B2 | 3/2015 | Wolf |
| 8,989,855 B2 | 3/2015 | Murphy |
| 9,031,658 B2 | 5/2015 | Chiao |
| 9,037,226 B2 | 5/2015 | Hacker |
| 9,078,671 B2 | 7/2015 | Beale |
| 9,084,550 B1 | 7/2015 | Bartol |
| 9,084,551 B2 | 7/2015 | Brunnett |
| 9,119,533 B2 | 9/2015 | Ghaffari |
| 9,121,423 B2 | 9/2015 | Sharpe |
| 9,149,188 B2 | 10/2015 | Eng |
| 9,155,503 B2 | 10/2015 | Cadwell |
| 9,204,830 B2 | 12/2015 | Zand |
| 9,247,952 B2 | 2/2016 | Bleich |
| 9,295,401 B2 | 3/2016 | Cadwell |
| 9,295,461 B2 | 3/2016 | Bojarski |
| 9,339,332 B2 | 5/2016 | Srivastava |
| 9,352,153 B2 | 5/2016 | Van Dijk |
| 9,370,654 B2 | 6/2016 | Scheiner |
| 9,579,503 B2 | 2/2017 | Mckinney |
| 9,616,233 B2 | 4/2017 | Shi |
| 9,622,684 B2 | 4/2017 | Wybo |
| 9,714,350 B2 | 7/2017 | Hwang |
| 9,730,634 B2 | 8/2017 | Cadwell |
| 9,788,905 B2 | 10/2017 | Avisar |
| 9,820,768 B2 | 11/2017 | Gee |
| 9,855,431 B2 | 1/2018 | Ternes |
| 9,913,594 B2 | 3/2018 | Li |
| 9,935,395 B1 | 4/2018 | Jepsen |
| 9,999,719 B2 | 6/2018 | Kitchen |
| 10,022,090 B2 | 7/2018 | Whitman |
| 10,039,461 B2 | 8/2018 | Cadwell |
| 10,039,915 B2 | 8/2018 | Mcfarlin |
| 10,092,349 B2 | 10/2018 | Engeberg |
| 10,154,792 B2 | 12/2018 | Sakai |
| 10,292,883 B2 | 5/2019 | Jepsen |
| 10,342,452 B2 | 7/2019 | Sterrantino |
| 10,349,862 B2 | 7/2019 | Sterrantino |
| 10,398,369 B2 | 9/2019 | Brown |
| 10,418,750 B2 | 9/2019 | Jepsen |
| 10,631,912 B2 | 4/2020 | Mcfarlin |
| 10,783,801 B1 | 9/2020 | Beaubien |
| 11,189,379 B2 | 11/2021 | Giataganas |
| 2001/0031916 A1 | 10/2001 | Bennett |
| 2001/0039949 A1 | 11/2001 | Loubser |
| 2001/0049524 A1 | 12/2001 | Morgan |
| 2001/0056280 A1 | 12/2001 | Underwood |
| 2002/0001995 A1 | 1/2002 | Lin |
| 2002/0001996 A1 | 1/2002 | Seki |
| 2002/0007129 A1 | 1/2002 | Marino |
| 2002/0007188 A1 | 1/2002 | Arambula |
| 2002/0055295 A1 | 5/2002 | Itai |
| 2002/0065481 A1 | 5/2002 | Cory |
| 2002/0072686 A1 | 6/2002 | Hoey |
| 2002/0095080 A1 | 7/2002 | Cory |
| 2002/0149384 A1 | 10/2002 | Reasoner |
| 2002/0161415 A1 | 10/2002 | Cohen |
| 2002/0183647 A1 | 12/2002 | Gozani |
| 2002/0193779 A1 | 12/2002 | Yamazaki |
| 2002/0193843 A1 | 12/2002 | Hill |
| 2002/0194934 A1 | 12/2002 | Taylor |
| 2003/0032966 A1 | 2/2003 | Foley |
| 2003/0045808 A1 | 3/2003 | Kaula |
| 2003/0078618 A1 | 4/2003 | Fey |
| 2003/0088185 A1 | 5/2003 | Prass |
| 2003/0105503 A1 | 6/2003 | Marino |
| 2003/0171747 A1 | 9/2003 | Kanehira |
| 2003/0199191 A1 | 10/2003 | Ward |
| 2003/0212335 A1 | 11/2003 | Huang |
| 2004/0019370 A1 | 1/2004 | Gliner |
| 2004/0034340 A1 | 2/2004 | Biscup |
| 2004/0068203 A1 | 4/2004 | Gellman |
| 2004/0135528 A1 | 7/2004 | Yasohara |
| 2004/0172114 A1 | 9/2004 | Hadzic |
| 2004/0199084 A1 | 10/2004 | Kelleher |
| 2004/0204628 A1 | 10/2004 | Rovegno |
| 2004/0225228 A1 | 11/2004 | Ferree |
| 2004/0229495 A1 | 11/2004 | Negishi |
| 2004/0230131 A1 | 11/2004 | Kassab |
| 2004/0260358 A1 | 12/2004 | Vaughan |
| 2005/0004593 A1 | 1/2005 | Simonson |
| 2005/0004623 A1 | 1/2005 | Miles |
| 2005/0075067 A1 | 4/2005 | Lawson |
| 2005/0075578 A1 | 4/2005 | Gharib |
| 2005/0080418 A1 | 4/2005 | Simonson |
| 2005/0085743 A1 | 4/2005 | Hacker |
| 2005/0119660 A1 | 6/2005 | Bourlion |
| 2005/0149143 A1 | 7/2005 | Libbus |
| 2005/0159659 A1 | 7/2005 | Sawan |
| 2005/0182454 A1 | 8/2005 | Gharib |
| 2005/0182456 A1* | 8/2005 | Ziobro ............... A61N 1/0531 607/48 |
| 2005/0215993 A1 | 9/2005 | Phan |
| 2005/0256582 A1 | 11/2005 | Ferree |
| 2005/0261559 A1 | 11/2005 | Mumford |
| 2006/0004424 A1 | 1/2006 | Loeb |
| 2006/0009754 A1 | 1/2006 | Boese |
| 2006/0025702 A1 | 2/2006 | Sterrantino |
| 2006/0025703 A1 | 2/2006 | Miles |
| 2006/0052828 A1 | 3/2006 | Kim |
| 2006/0069315 A1 | 3/2006 | Miles |
| 2006/0085048 A1 | 4/2006 | Cory |
| 2006/0085049 A1 | 4/2006 | Cory |
| 2006/0122514 A1 | 6/2006 | Byrd |
| 2006/0173383 A1 | 8/2006 | Esteve |
| 2006/0200023 A1 | 9/2006 | Melkent |
| 2006/0241725 A1 | 10/2006 | Libbus |
| 2006/0258951 A1 | 11/2006 | Bleich |
| 2006/0264777 A1 | 11/2006 | Drew |
| 2006/0276702 A1 | 12/2006 | McGinnis |
| 2006/0292919 A1 | 12/2006 | Kruss |
| 2007/0016097 A1 | 1/2007 | Farquhar |
| 2007/0021682 A1 | 1/2007 | Gharib |
| 2007/0032841 A1 | 2/2007 | Urmey |
| 2007/0049962 A1 | 3/2007 | Marino |
| 2007/0097719 A1 | 5/2007 | Parramon |
| 2007/0184422 A1 | 8/2007 | Takahashi |
| 2007/0270918 A1 | 11/2007 | De Bel |
| 2007/0282217 A1 | 12/2007 | McGinnis |
| 2008/0015612 A1 | 1/2008 | Urmey |
| 2008/0027507 A1 | 1/2008 | Bijelic |
| 2008/0039174 A1 | 2/2008 | Cory |
| 2008/0058606 A1 | 3/2008 | Miles |
| 2008/0064976 A1 | 3/2008 | Kelleher |
| 2008/0065144 A1 | 3/2008 | Marino |
| 2008/0065178 A1 | 3/2008 | Kelleher |
| 2008/0071191 A1 | 3/2008 | Kelleher |
| 2008/0077198 A1 | 3/2008 | Webb |
| 2008/0082136 A1 | 4/2008 | Gaudiani |
| 2008/0097164 A1 | 4/2008 | Miles |
| 2008/0167574 A1 | 7/2008 | Farquhar |
| 2008/0183190 A1 | 7/2008 | Adcox |
| 2008/0183915 A1 | 7/2008 | Iima |
| 2008/0194970 A1 | 8/2008 | Steers |
| 2008/0214903 A1 | 9/2008 | Orbach |
| 2008/0218393 A1 | 9/2008 | Kuramochi |
| 2008/0254672 A1 | 10/2008 | Dennes |
| 2008/0269777 A1 | 10/2008 | Appenrodt |
| 2008/0281313 A1 | 11/2008 | Fagin |
| 2008/0300650 A1 | 12/2008 | Gerber |
| 2008/0306348 A1 | 12/2008 | Kuo |
| 2009/0018399 A1 | 1/2009 | Martinelli |
| 2009/0088660 A1 | 4/2009 | McMorrow |
| 2009/0105604 A1 | 4/2009 | Bertagnoli |
| 2009/0143797 A1 | 6/2009 | Smith |
| 2009/0177112 A1 | 7/2009 | Gharib |
| 2009/0182322 A1 | 7/2009 | D Amelio |
| 2009/0197476 A1 | 8/2009 | Wallace |

(56) References Cited

U.S. PATENT DOCUMENTS

| | | |
|---|---|---|
| 2009/0204016 A1 | 8/2009 | Gharib |
| 2009/0209879 A1 | 8/2009 | Kaula |
| 2009/0221153 A1 | 9/2009 | Santangelo |
| 2009/0240117 A1 | 9/2009 | Chmiel |
| 2009/0259108 A1 | 10/2009 | Miles |
| 2009/0279767 A1 | 11/2009 | Kukuk |
| 2009/0281595 A1 | 11/2009 | King |
| 2009/0299439 A1 | 12/2009 | Mire |
| 2010/0004949 A1 | 1/2010 | O'Brien |
| 2010/0036280 A1 | 2/2010 | Ballegaard |
| 2010/0036384 A1 | 2/2010 | Gorek |
| 2010/0049188 A1 | 2/2010 | Nelson |
| 2010/0106011 A1 | 4/2010 | Byrd |
| 2010/0152604 A1 | 6/2010 | Kaula |
| 2010/0152811 A1 | 6/2010 | Flaherty |
| 2010/0152812 A1 | 6/2010 | Flaherty |
| 2010/0160731 A1 | 6/2010 | Giovannini |
| 2010/0168561 A1 | 7/2010 | Anderson |
| 2010/0191311 A1 | 7/2010 | Scheiner |
| 2010/0286554 A1 | 11/2010 | Davis |
| 2010/0317989 A1 | 12/2010 | Gharib |
| 2011/0004207 A1 | 1/2011 | Wallace |
| 2011/0028860 A1 | 2/2011 | Chenaux |
| 2011/0071418 A1 | 3/2011 | Stellar |
| 2011/0082383 A1 | 4/2011 | Cory |
| 2011/0160731 A1 | 6/2011 | Bleich |
| 2011/0184308 A1 | 7/2011 | Kaula |
| 2011/0230734 A1 | 9/2011 | Fain |
| 2011/0230782 A1 | 9/2011 | Bartol |
| 2011/0245647 A1 | 10/2011 | Stanislaus |
| 2011/0270120 A1 | 11/2011 | Mcfarlin |
| 2011/0270121 A1 | 11/2011 | Johnson |
| 2011/0295579 A1 | 12/2011 | Tang |
| 2011/0313530 A1 | 12/2011 | Gharib |
| 2012/0004516 A1 | 1/2012 | Eng |
| 2012/0071784 A1 | 3/2012 | Melkent |
| 2012/0109000 A1 | 5/2012 | Kaula |
| 2012/0109004 A1 | 5/2012 | Cadwell |
| 2012/0220891 A1 | 8/2012 | Kaula |
| 2012/0238893 A1 | 9/2012 | Farquhar |
| 2012/0245439 A1 | 9/2012 | Andre |
| 2012/0277780 A1 | 11/2012 | Smith |
| 2012/0296230 A1 | 11/2012 | Davis |
| 2013/0027186 A1 | 1/2013 | Cinbis |
| 2013/0030257 A1 | 1/2013 | Nakata |
| 2013/0090641 A1 | 4/2013 | Mckinney |
| 2013/0245722 A1 | 9/2013 | Ternes |
| 2013/0261422 A1 | 10/2013 | Gilmore |
| 2013/0267874 A1 | 10/2013 | Marcotte |
| 2014/0058284 A1 | 2/2014 | Bartol |
| 2014/0073985 A1 | 3/2014 | Sakai |
| 2014/0074084 A1 | 3/2014 | Engeberg |
| 2014/0088463 A1 | 3/2014 | Wolf |
| 2014/0121555 A1 | 5/2014 | Scott |
| 2014/0275914 A1 | 9/2014 | Li |
| 2014/0275926 A1 | 9/2014 | Scott |
| 2014/0288389 A1 | 9/2014 | Gharib |
| 2014/0303452 A1 | 10/2014 | Ghaffari |
| 2015/0012066 A1 | 1/2015 | Underwood |
| 2015/0088029 A1 | 3/2015 | Wybo |
| 2015/0088030 A1 | 3/2015 | Taylor |
| 2015/0112325 A1 | 4/2015 | Whitman |
| 2015/0202395 A1 | 7/2015 | Fromentin |
| 2015/0238260 A1 | 8/2015 | Nau, Jr. |
| 2015/0250423 A1 | 9/2015 | Hacker |
| 2015/0311607 A1 | 10/2015 | Ding |
| 2015/0380511 A1 | 12/2015 | Irsigler |
| 2016/0000382 A1 | 1/2016 | Jain |
| 2016/0015299 A1 | 1/2016 | Chan |
| 2016/0038072 A1 | 2/2016 | Brown |
| 2016/0038073 A1 | 2/2016 | Brown |
| 2016/0038074 A1 | 2/2016 | Brown |
| 2016/0135834 A1 | 5/2016 | Bleich |
| 2016/0174861 A1 | 6/2016 | Cadwell |
| 2016/0199659 A1 | 7/2016 | Jiang |
| 2016/0235999 A1 | 8/2016 | Nuta |
| 2016/0262699 A1 | 9/2016 | Goldstone |
| 2016/0270679 A1 | 9/2016 | Mahon |
| 2016/0287112 A1 | 10/2016 | Mcfarlin |
| 2016/0287861 A1 | 10/2016 | Mcfarlin |
| 2016/0317053 A1 | 11/2016 | Srivastava |
| 2016/0339241 A1 | 11/2016 | Hargrove |
| 2017/0056643 A1 | 3/2017 | Herb |
| 2017/0231508 A1 | 8/2017 | Edwards |
| 2017/0273592 A1 | 9/2017 | Sterrantino |
| 2018/0345004 A1 | 12/2018 | Mcfarlin |
| 2019/0180637 A1 | 6/2019 | Mealer |
| 2019/0350485 A1 | 11/2019 | Sterrantino |

FOREIGN PATENT DOCUMENTS

| | | |
|---|---|---|
| AU | 2006217448 A1 | 8/2006 |
| AU | 2003232111 B2 | 10/2008 |
| AU | 2004263152 B2 | 8/2009 |
| AU | 2005269287 B2 | 5/2011 |
| AU | 2008236665 B2 | 8/2013 |
| AU | 2012318436 A1 | 4/2014 |
| AU | 2016244152 A1 | 11/2017 |
| AU | 2016244152 B2 | 12/2018 |
| AU | 2019201702 A1 | 4/2019 |
| BR | 9604655 C1 | 12/1999 |
| BR | 0609144 A2 | 2/2010 |
| CA | 2144211 C | 5/2005 |
| CA | 2229391 C | 9/2005 |
| CA | 2574845 A1 | 2/2006 |
| CA | 2551185 C | 10/2007 |
| CA | 2662474 A1 | 3/2008 |
| CA | 2850784 A1 | 4/2013 |
| CA | 2769658 C | 1/2016 |
| CA | 2981635 A1 | 10/2016 |
| CN | 101018585 A | 8/2007 |
| CN | 100571811 C | 12/2009 |
| CN | 104066396 A | 9/2014 |
| CN | 103052424 B | 12/2015 |
| CN | 104080509 B | 9/2017 |
| CN | 104717996 B | 1/2018 |
| CN | 107666939 A | 2/2018 |
| CN | 111419179 A | 7/2020 |
| DE | 2753109 A1 | 6/1979 |
| DE | 2831313 A1 | 2/1980 |
| DE | 8803153 U1 | 6/1988 |
| DE | 3821219 C1 | 8/1989 |
| DE | 29510204 U1 | 8/1995 |
| DE | 19530869 A1 | 2/1997 |
| DE | 29908259 U1 | 7/1999 |
| DE | 19921279 C1 | 11/2000 |
| DE | 19618945 C2 | 2/2003 |
| EP | 0161895 A2 | 11/1985 |
| EP | 298268 | 1/1989 |
| EP | 0719113 A1 | 7/1996 |
| EP | 0759307 A2 | 2/1997 |
| EP | 0836514 A2 | 4/1998 |
| EP | 890341 | 1/1999 |
| EP | 972538 | 1/2000 |
| EP | 1656883 A1 | 5/2006 |
| EP | 1115338 B1 | 8/2006 |
| EP | 1804911 | 7/2007 |
| EP | 1804911 A1 | 7/2007 |
| EP | 1534130 A4 | 9/2008 |
| EP | 1441530 B1 | 4/2010 |
| EP | 1804911 B1 | 1/2012 |
| EP | 2481338 A3 | 9/2012 |
| EP | 2763616 A1 | 8/2014 |
| EP | 1385417 B1 | 4/2016 |
| EP | 1680177 B1 | 4/2017 |
| EP | 3277366 B1 | 12/2021 |
| ES | 2725489 T3 | 9/2019 |
| FI | 73878 C | 12/1987 |
| FR | 2624373 A1 | 6/1989 |
| FR | 2624748 B1 | 10/1995 |
| FR | 2796846 A1 | 2/2001 |
| FR | 2795624 B1 | 9/2001 |
| FR | 2835732 B1 | 11/2004 |
| GB | 1534162 A | 11/1978 |

(56) References Cited

FOREIGN PATENT DOCUMENTS

| | | |
|---|---|---|
| GB | 2049431 A | 12/1980 |
| GB | 2052994 A | 2/1981 |
| GB | 2452158 A | 2/2009 |
| GB | 2519302 B | 4/2016 |
| IT | 1221615 B | 7/1990 |
| JP | H0723964 A | 1/1995 |
| JP | 2000028717 A | 1/2000 |
| JP | 3188437 B2 | 7/2001 |
| JP | 2000590531 A | 8/2003 |
| JP | 2003524452 A | 8/2003 |
| JP | 2004522497 A | 7/2004 |
| JP | 2008508049 A | 3/2008 |
| JP | 4295086 B2 | 7/2009 |
| JP | 4773377 B2 | 9/2011 |
| JP | 4854900 B2 | 1/2012 |
| JP | 4987709 B2 | 7/2012 |
| JP | 5132310 B2 | 1/2013 |
| JP | 2014117328 A | 6/2014 |
| JP | 2014533135 A | 12/2014 |
| JP | 6145916 B2 | 6/2017 |
| JP | 2018514258 A | 6/2018 |
| JP | 6749338 B2 | 9/2020 |
| KR | 100632980 B1 | 10/2006 |
| KR | 1020070106675 A | 11/2007 |
| KR | 100877229 B1 | 1/2009 |
| KR | 20140074973 A | 6/2014 |
| KR | 1020170133499 A | 12/2017 |
| KR | 102092583 B1 | 3/2020 |
| KR | 1020200033979 A | 3/2020 |
| NZ | 541889 A | 4/2010 |
| SE | 467561 B | 8/1992 |
| SE | 508357 C2 | 9/1998 |
| WO | 1999037359 A1 | 7/1999 |
| WO | 2000038574 A1 | 7/2000 |
| WO | 2000066217 A1 | 11/2000 |
| WO | 2001037728 A1 | 5/2001 |
| WO | 2001078831 A2 | 10/2001 |
| WO | 2001087154 A1 | 11/2001 |
| WO | 2001093748 A2 | 12/2001 |
| WO | 2002082982 A1 | 10/2002 |
| WO | 2003005887 A2 | 1/2003 |
| WO | 2003034922 A1 | 5/2003 |
| WO | 2003094744 A1 | 11/2003 |
| WO | 2004064632 A1 | 8/2004 |
| WO | 2005030318 A1 | 4/2005 |
| WO | 2006015069 A1 | 2/2006 |
| WO | 2006026482 A2 | 3/2006 |
| WO | 2006042241 A2 | 4/2006 |
| WO | 2006113394 A2 | 10/2006 |
| WO | 2008002917 A2 | 1/2008 |
| WO | 2008005843 A2 | 1/2008 |
| WO | 2008097407 A2 | 8/2008 |
| WO | 2009051965 A1 | 4/2009 |
| WO | 2010090835 A1 | 8/2010 |
| WO | 2011014598 A1 | 2/2011 |
| WO | 2011150502 A2 | 12/2011 |
| WO | 2013019757 A2 | 2/2013 |
| WO | 2013052815 A1 | 4/2013 |
| WO | 2013151770 A1 | 10/2013 |
| WO | 2015069962 A1 | 5/2015 |
| WO | 2016160477 A1 | 10/2016 |

OTHER PUBLICATIONS

International Search Report for PCT/US2005/026692, dated Nov. 16, 2005.
International Search Report for PCT/US2016/023903, dated Sep. 6, 2016.
Cadwell et al. "Electrophysiologic Equipment and Electrical Safety" Chapter 2, Electrodiagnosis in Clinical Neurology, Fourth Edition; Churchill Livingstone, p. 15, 30-31; 1999.
Ott, "Noise Reduction Techniques in Electronic Systems" Second Edition; John Wiley & Sons, p. 62, 1988.
Stecker et al. "Strategies for minimizing 60 Hz pickup during evoked potential recording", Electroencephalography and clinical Neurophysiology 100 (1996) 370-373.
Wood et al. "Comparative analysis of power-line interference between two- or three-electrode biopotential amplifiers" Biomedical Engineering, Med. & Biol. Eng. & Comput., 1995, 33, 63-68.
Clements, et al., "Evoked and Spontaneous Electromyography to Evaluate Lumbosacral Pedicle Screw Placement", 21 (5):600-604 (1996).
Danesh-Clough, et al., "The Use of Evoked EMG in Detecting Misplaced Thoracolumbar Pedicle Screws", 26(12):1313-1316 (2001).
Dezawa et al., "Retroperitoneal Laparoscopic Lateral Approach to the Lumbar Spine: A New Approach, Technique, and Clinical Trial", Journal of Spinal Disorders 13(2):138-143 (2000).
Dickman, et al., "Techniques in Neurosurgery", National Library of Medicine, 3 (4) 301-307 (1997).
Epstein, et al., "Evaluation of Intraoperative Somatosensory-Evoked Potential Monitoring During 100 Cervical Operations", 18(6):737-747 (1993), J.B. Lippincott Company.
Glassman, et al., "A Prospective Analysis of Intraoperative Electromyographic Monitoring of Pedicle Screw Placement with Computed Tomographic Scan Confirmation", 20(12):1375-1379.
Goldstein, et al., "Minimally Invasive Endoscopic Surgery of the Lumbar Spine", Operative Techniques in Orthopaedics, 7 (1):27-35 (1997).
Greenblatt, et al., "Needle Nerve Stimulator-Locator", 41 (5):599-602 (1962).
H.M. Mayer, "Minimally Invasive Spine Surgery, A Surgical Manual", Chapter 12, pp. 117-131 (2000).
Hinrichs, et al., "A trend-detection algorithm for intraoperative EEG monitoring", Med. Eng. Phys. 18 (8):626-631 (1996).
Bergey et al., "Endoscopic Lateral Transpsoas Approach to the Lumbar Spine", SPINE 29 (15):1681-1688 (2004).
Holland, "Spine Update, Intraoperative Electromyography During Thoracolumbar Spinal Surgery", 23 (17):1915-1922 (1998).
Holland, et al., "Continuous Electromyographic Monitoring to Detect Nerve Root Injury During Thoracolumbar Scoliosis Surgery", 22 (21):2547-2550 (1997), Lippincott-Raven Publishers.
Hovey, A Guide to Motor Nerve Monitoring, pp. 1-31 Mar. 20, 1998, The Magstim Company Limited.
Kevin T. Foley, et al., "Microendoscipic Discectomy" Techniques in Neurosurgery, 3:(4):301-307, © 1997 Lippincott-Raven Publishers, Philadelphia.
Kossmann et al., "The use of a retractor system (SynFrame) for open, minimal invasive reconstruction of the anterior column of the thoracic and lumbar spine", 10:396-402 (2001).
Kossmann, et. al., "Minimally Invasive Vertebral Replacement with Cages in Thoracic and Lumbar Spine", European Journal of Trauma, 2001, No. 6, pp. 292-300.
Lenke, et. al., "Triggered Electromyographic Threshold for Accuracy of Pedicle Screw Placement, An Animal Model and Clinical Correlation", 20 (14):1585-1591 (1995).
Lomanto et al., "7th World Congress of Endoscopic Surgery" Singapore, Jun. 1-4, 2000 Monduzzi Editore S.p.A.; email: monduzzi@monduzzi.com, pp. 97-103 and 105-111.
MaGuire, et. al., "Evaluation of Intrapedicular Screw Position Using Intraoperative Evoked Electromyography", 20 (9):1068-1074 (1995).
Mathews et al., "Laparoscopic Discectomy With Anterior Lumbar Interbody Fusion, A Preliminary Review", 20 (16):1797-1802, (1995), Lippincott-Raven Publishers.
Bertagnoli, et. al., "The AnteroLateral transPsoatic Approach (ALPA), A New Technique for Implanting Prosthetic Disc-Nucleus Devices", 16 (4):398-404 (2003).
Michael R. Isley, et. al., "Recent Advances in Intraoperative Neuromonitoring of Spinal Cord Function: Pedicle Screw Stimulation Techniques", Am. J. End Technol. 37:93-126 (1997).
Minahan, et. al., "The Effect of Neuromuscular Blockade on Pedicle Screw Stimulation Thresholds" 25(19):2526-2530 (2000).
Pimenta et. al., "Implante de prótese de núcleo pulposo: análise inicial", J Bras Neurocirurg 12(2):93-96, (2001).

(56) References Cited

OTHER PUBLICATIONS

Raymond J. Gardocki, MD, "Tubular diskectomy minimizes collateral damage", AAOS Now, Sep. 2009 Issue, http://www.aaos.org/news/aaosnow/sep09/clinical12.asp.

Raymond, et. al., "The NerveSeeker: A System for Automated Nerve Localization", Regional Anesthesia 17:151-162 (1992).

Reidy, et. al., "Evaluation of electromyographic monitoring during insertion of thoracic pedicle screws", British Editorial Society of Bone and Joint Surgery 83 (7):1009-1014, (2001).

Rose et al., "Persistently Electrified Pedicle Stimulation Instruments in Spinal Instrumentation: Technique and Protocol Development", Spine: 22(3): 334-343 (1997).

Teresa Riordan "Patents; A businessman invents a device to give laparoscopic surgeons a better view of their work", New York Times www.nytimes.com/2004/29/business/patents-businessman-invents-device-give-la (Mar. 2004).

Toleikis, et. al., "The usefulness of Electrical Stimulation for Assessing Pedicle Screw Placements", Journal of Spinal Disorders, 13 (4):283-289 (2000).

U.Schick, et. al., "Microendoscopic lumbar discectomy versus open surgery: an intraoperative EMG study", pp. 20-26, Published online: Jul. 31, 2001 © Springer-Verlag 2001.

Bose, et. al., "Neurophysiologic Monitoring of Spinal Nerve Root Function During Instrumented Posterior Lumbar Spine Surgery", 27 (13):1440-1450 (2002).

Vaccaro, et. al., "Principles and Practice of Spine Surgery", Mosby, Inc. © 2003, Chapter 21, pp. 275-281.

Vincent C. Traynelis, "Spinal arthroplasty", Neurosurg Focus 13 (2):1-7. Article 10, (2002).

Welch, et. al., "Evaluation with evoked and spontaneous electromyography during lumbar instrumentation: a prospective study", J Neurosurg 87:397-402, (1997).

Zouridakis, et. al., "A Concise Guide to Intraoperative Monitoring", Library of Congress card No. 00-046750, Chapter 3, p. 21, chapter 4, p. 58 and chapter 7 pp. 119-120.

Medtronic, "Nerve Integrity Monitor, Intraoperative EMG Monitor, User's Guide", Medtronic Xomed U.K. Ltd., Unit 5, West Point Row, Great Park Road, Almondsbury, Bristol B5324QG, England, pp. 1-39.

Chapter 9, "Root Finding and Nonlinear Sets of Equations", Chapter 9:350-354, http://www.nr.com.

Digitimer LTD., 37 Hydeway, Welwyn Garden City, Hertfordshire. AL7 3BE England, email:sales@digitimer.com, website: www.digitimer.com, "Constant Current High Voltage Stimulator, Model DS7A, for Percutaneous Stimulation of Nerve and Muscle Tissue".

Ford et al, Electrical characteristics of peripheral nerve stimulators, implications for nerve localization, Dept. of Anesthesia, University of Cincinnati College of Medicine, Cincinnati, OH 45267, pp. 73-77.

Deletis et al., "The role of intraoperative neurophysiology in the protection or documentation of surgically induced injury to the spinal cord", Correspondence Address: Hyman Newman Institute for Neurology & Neurosurgery, Beth Israel Medical Center, 170 East End Ave., Room 311, NY 10128.

Butterworth et. al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.

Calancie, et. al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).

Calancie, et. al., "Threshold-level repetitive transcranial electrical stimulation for intraoperative monitoring of central motor conduction", J. Neurosurg 95:161-168 (2001).

Calancie, et. al., Stimulus-Evoked EMG Monitoring During Transpedicular Lumbosacral Spine Instrumentation, Initial Clinical Results, 19 (24):2780-2786 (1994).

Carl T. Brighton, "Clinical Orthopaedics and Related Research", Clinical Orthopaedics and related research No. 384, pp. 82-100 (2001).

Aage R. Møller, "Intraoperative Neurophysiologic Monitoring", University of Pittsburgh, School of Medicine Pennsylvania, © 1995 by Harwood Academic Publishers GmbH.

Urmey "Using the nerve stimulator for peripheral or plexus nerve blocks" Minerva Anesthesiology 2006; 72:467-71.

\* cited by examiner

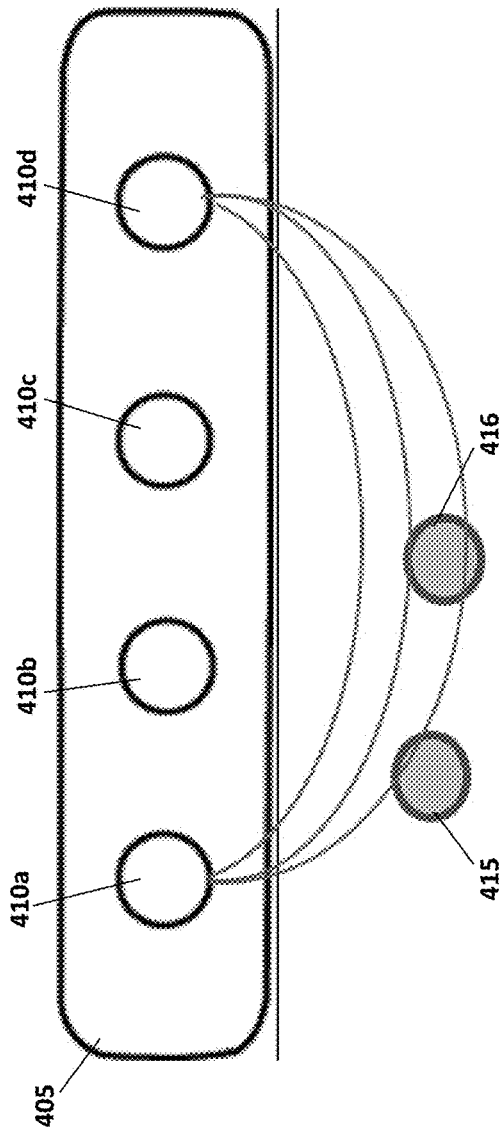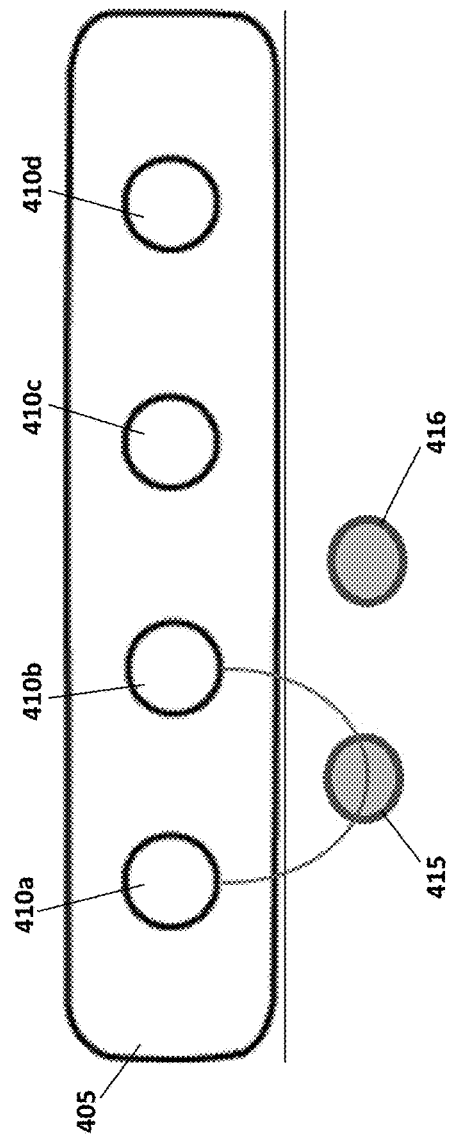

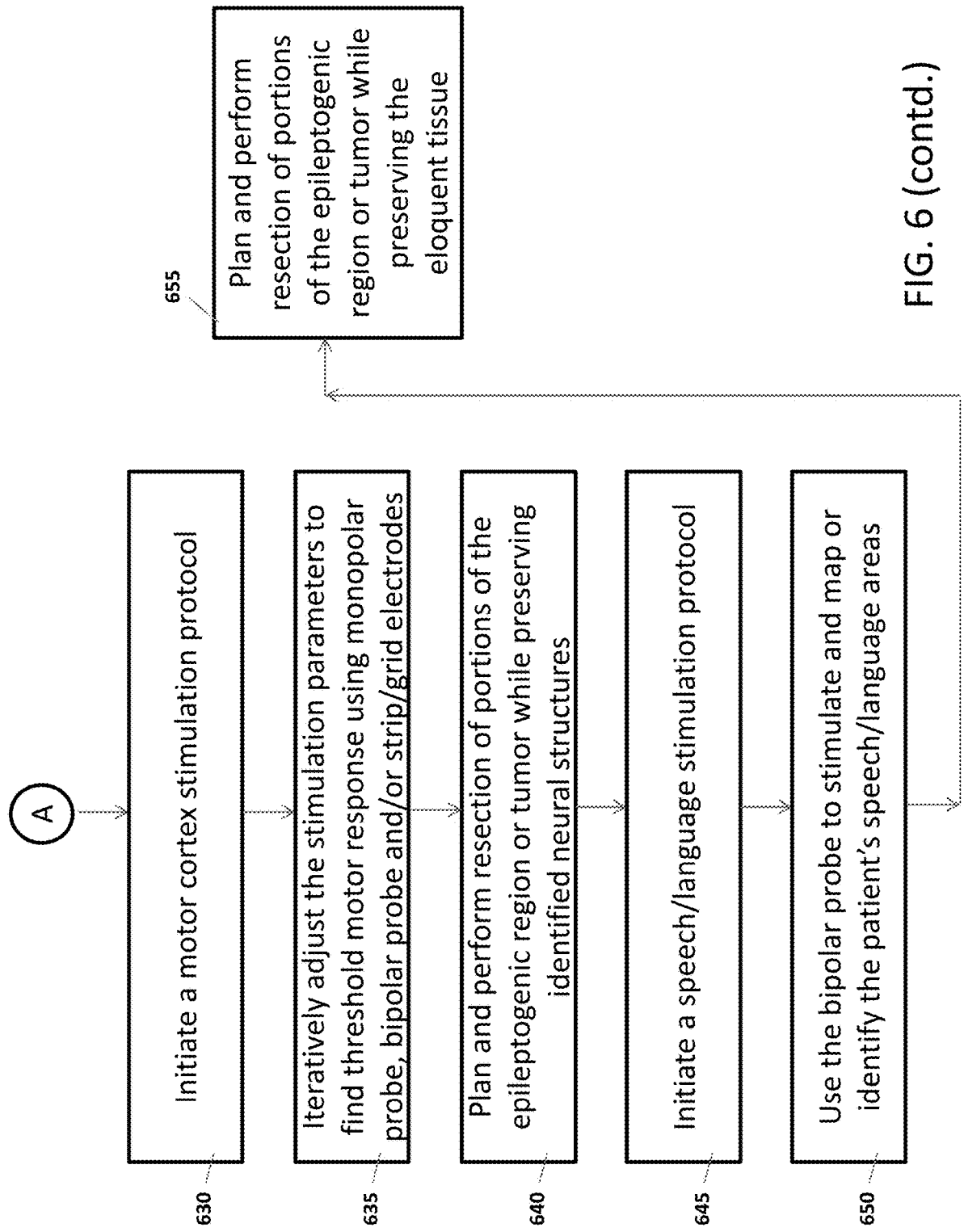
FIG. 6 (contd.)

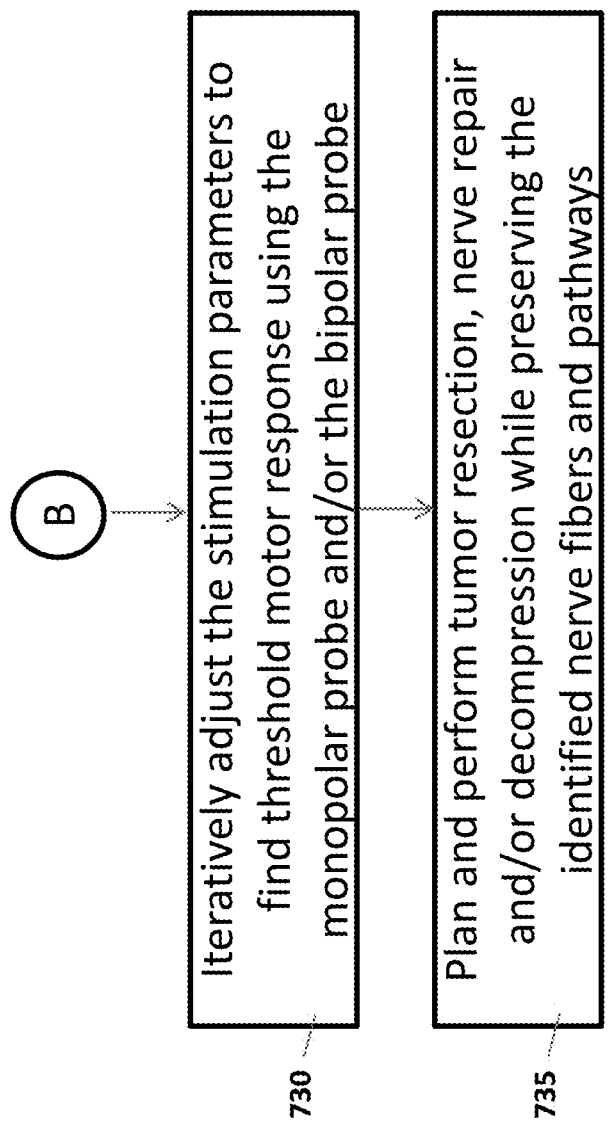
FIG. 7 (contd.)

SYSTEMS AND METHODS FOR DYNAMIC NEUROPHYSIOLOGICAL STIMULATION

CROSS-REFERENCE

The present application relies on U.S. Provisional Patent Application No. 62/666,959, entitled "Systems and Methods for Neurophysiological Stimulation" and filed on May 4, 2018, for priority, which is hereby incorporated herein by reference in its entirety.

FIELD

The present specification is related generally to the field of neurophysiological stimulation. More specifically the present specification is related to a stimulation module that enables user-preferred selection of one or any combination of a plurality of low current stimulation outputs or channels.

BACKGROUND

Intraoperative neurophysiological monitoring (IONM) is directed towards identifying, mapping and monitoring neural structures in accordance with their functions with a goal of preserving the structural integrity of these neural structures during physically invasive procedures such as surgery.

In some methods, identifying, mapping and monitoring neural structures comprises applying electrical stimulation at or near an area where the target neural structures are believed to be located. Application of the electrical stimulation is transmitted through the nervous system structures to excite or depress the associated response(s) or function(s). For example, an electrical impulse is generated in the muscle(s), as a result of the excitation, that can be sensed using recording electrodes, thereby indicating presence and functionality of a neural structure to a surgeon. For example, cortical stimulation mapping (CSM) is a type of electrocorticography that involves a physically invasive procedure and aims to localize the function of specific brain regions through direct electrical stimulation of the cerebral cortex.

Prior art nerve integrity monitoring systems pose limitations when used across varied surgical procedures and accompanied neuro-stimulation scenarios. As an example, a critical limitation of majority of prior art nerve integrity monitoring systems is the availability of a limited number of low current outputs or channels for delivering stimulation to a plurality of neural regions thereby limiting the ability to simultaneously stimulate multiple nerves or multiple branches of single nerves. For example, the ES-IX stimulator, from Cadwell Industries Inc., also the Applicant of the present specification, has a maximum of one low current stimulation output. Such limitation necessitates frequent manual intervention, such as having to move the connections of stimulation components (for example, electrodes and probes) to change the location of the delivered stimulus on a patient's anatomy.

Another drawback of prior art nerve integrity monitoring systems is that these are not designed to provide electrical stimulation of sufficient amplitude to elicit excitation activity of the muscles. Another limitation is a lack of integration of the stimulators with a multi-modality monitoring system. For example, the Nicolet® Cortical Stimulator supports recording of only electroencephalography and connection of a single probe (bipolar). The Inomed® stimulator also supports connection of a single probe.

As a result of these limitations, prior art nerve integrity monitoring systems are associated with various disadvantages including the need for additional operational steps which increase the duration of the surgical procedures to the detriment of patients and medical personnel, increased complexity and confusion associated with intraoperative neural monitoring, a need for greater human and/or mechanical intervention and an inability to efficiently integrate multiple neural stimulation and monitoring modalities.

Thus, there is a need for systems and methods that enable a user to select all or any combination of multiple stimulation modalities available to the user. There is also a need to enable the user to stimulate the neurological system with minimal, less frequent and more streamlined manual or electromechanical intervention.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a method of using cortical stimulation to identify and assess neural structures during a surgical procedure, the method comprising: providing an intraoperative neurophysiological monitoring (IONM) system comprising at least one probe, at least one reference electrode, at least one strip electrode or grid electrode, at least one sensing electrode, and a stimulation module; placing the at least one reference electrode in a perimeter of a surgical field of a patient; positioning the at least one probe and/or the at least one strip electrode or grid electrode at target locations on the anatomy of said patient; preparing for recordation of said patient's responses to stimulation by positioning said at least one sensing electrode on said patient's anatomy; initiating a stimulation protocol; adjusting stimulation parameters of the stimulation protocol to determine a threshold response; and identifying or assessing the neural structures based on said threshold response, wherein assessing comprises determining if the patient's anatomy is functioning in a manner indicative of an underlying disease or, alternatively, is functioning in a non-pathological manner.

Optionally, the stimulation protocol is a motor cortex stimulation protocol, a speech stimulation protocol, or a language stimulation protocol.

Optionally, said stimulation module comprises a first plurality of output connectors and a second plurality of probe ports. Optionally, the first plurality of output connectors comprise at least 12 output connectors. Optionally, the first plurality of output connectors are configured to enable connection to the at least one strip electrode or grid electrode, wherein the at least one strip electrode or grid electrode has a plurality of contacts and wherein a total number of the plurality of contacts does not exceed a total number of the first plurality of output connectors. Optionally, the second plurality of probe ports comprises a first probe port and a second probe port, wherein each of the first probe port and the second probe port is configured to connect to the at least one probe, wherein the at least one probe comprises passive probes, and wherein the passive probes comprise at least one of a monopolar probe or a bipolar probe. Optionally, each of the plurality of output connectors are configurable as either an anode or a cathode through a user interface in data communication with the IONM system. Optionally, the method further comprises providing a user interface in data communication with the IONM system, receiving, via the user interface, user-defined stimuli, and delivering signals representative of the user-defined stimuli to pairs of the plurality of output connectors, each of the plurality of output connectors being configurable as either an anode or a cathode through the user interface. Optionally, the second plurality of probe ports comprises a probe port adapted to connect the at least one probe, wherein the at least one probe comprises an anode and a cathode and wherein the probe port comprises first and second outputs for connection of to the anode and the cathode of the at least one probe, a first pair of connection ports adapted to connect to a power supply and a second pair of connection ports adapted to connect to a communication module.

Optionally, the at least one sensing electrode comprises an electromyography needle electrode.

Optionally, the stimulation protocol comprises a multi-pulse train having 2 to 10 pulses wherein each of the pulses is defined by a pulse width in a range of 50 μsec to 1000 μsec, an inter-stimulus interval in a range of 0.5 to 10 milliseconds and a pulse amplitude in a range of 0.01 mA to 20 mA.

The present specification also discloses a method of using direct nerve stimulation to identify nerve fibers and nerve pathways during a surgical procedure, the method comprising: providing an intraoperative neurophysiological monitoring (IONM) system comprising at least one probe, at least one sensing electrode, and a stimulation module, wherein the stimulation module comprises at least twelve output connectors and a plurality of probe ports; positioning the at least one probe at a first target location on the patient; positioning the at least one sensing electrode at a second target location in the patient; initiating a direct nerve stimulation protocol; adjusting stimulation parameters of the direct nerve stimulation protocol to determine a threshold motor response; and identifying the nerve fibers and nerve pathways based on the threshold motor response.

Optionally, the IONM system further comprises at least one strip electrode or grid electrode having a total number of contacts not exceeding a total number of the at least twelve output connectors, wherein the at least twelve output connectors are adapted to connect to the at least one strip electrode or grid electrode.

Optionally, the plurality of probe ports comprises a first probe port and a second probe port and is configured to connect to the at least one probe, wherein the at least one probe comprises at least one passive monopolar probe or passive bipolar probe.

Optionally, each of the at least twelve output connectors are configurable as either an anode or a cathode.

Optionally, the method further comprises providing a user interface in data communication with the IONM system, receiving, via the user interface, user-defined stimuli, and delivering signals representative of the user-defined stimuli to pairs of the plurality of output connectors, each of the plurality of output connectors being configurable as either an anode or a cathode through the user interface.

Optionally, the plurality of probe ports comprises a probe port configured to connect to the at least one probe, wherein the at least one probe comprises an anode connection and a cathode connection, and wherein the probe port comprises first and second outputs adapted to connect to the anode and the cathode of the probe port, a first pair of connection ports adapted to connect to a power supply and a second pair of connection ports adapted to connect to a transceiver.

Optionally, the at least one sensing electrode comprises an electromyography needle electrode.

Optionally, the direct nerve stimulation protocol comprises a single pulse stimulation, wherein the single pulse has a frequency of 0.05 Hz to 90 Hz, a pulse width of 50 μsec to 1000 μsec, an interval between pulses of 0.5 millisecond to 10 milliseconds and a pulse amplitude in a range of 0.01 mA to 20 mA, with 2 mA or less for cranial nerves and 5 mA or less for peripheral nerves.

Optionally, the IONM system further comprises a handle having a proximal end configured to connect to the stimulation module and a distal end configured to attach to the at least one probe. Optionally, the handle comprises a first visual indicator, a second visual indicator, and an actuator configured to manually or automatically switch the stimulation module between a first mode of operation and a second mode operation depending upon a type of the at least one probe. Optionally, first visual indicator is configured to indicate at least one of the first mode of operation, the second mode of operation, a connection state of the at least one probe or what part of the at least one probe is active. Optionally, the second visual indicator provides a first indication signifying that a site of stimulation is at a first distance from a nerve and a second indication signifying that the site of stimulation is at a second distance from the nerve, wherein the first distance is less than the second distance.

The present specification also discloses a method of using cortical stimulation to identify neural structures during a surgical procedure, the method comprising: providing an intraoperative neurophysiological monitoring (IONM) system comprising at least one probe, at least one reference electrode, at least one strip or grid electrode, at least one sensing electrode, and a stimulation module; placing said at least one reference electrode in a perimeter of a surgical field of a patient; positioning said at least one probe and said at least ones strip or grid electrode at target locations on the anatomy of said patient; preparing for recordation of said patient's responses to stimulation by positioning said at least one sensing electrode on said patient's anatomy; initiating a stimulation protocol; adjusting stimulation parameters of said stimulation protocol to determine a threshold response; and identifying said neural structures based on said threshold response.

Optionally, the stimulation protocol is a motor cortex stimulation protocol, a speech stimulation protocol, or a language stimulation protocol.

Optionally, said stimulation module comprises a first plurality of twelve output connectors and a second plurality of probe ports.

Optionally, said twelve output connectors enable connection to said at least one strip or grid electrode having multiple contacts not exceeding said twelve output connectors.

Optionally, said plurality of probe ports comprises a first probe port and a second probe port and enables connection to said at least one probe, wherein said at least one probe comprises passive and smart probes, and wherein said passive probes include monopolar and bipolar probes.

Optionally, each of the twelve output connectors are configurable as either an anode or a cathode allowing user-defined stimuli to be delivered to arbitrary anode and cathode pairs.

Optionally, said second plurality of probe ports further comprises a third probe port, said third probe port configured for connecting a smart probe and comprising a pair of outputs for connection of an anode and a cathode of said smart probe and a first connection port for power and a second connection port for communications.

Optionally, said at least one sensing electrode includes an EMG needle electrode.

Optionally, said stimulation protocol comprises a multi-pulse train of 3 to 5 pulses, a pulse width of 500 μsec, an inter-stimulus interval of 2 to 4 milliseconds and a pulse amplitude of up to 20 mA.

The present specification also discloses a method of using direct nerve stimulation to identify nerve fibers and pathways during a surgical procedure, the method comprising: providing an intraoperative neurophysiological monitoring (IONM) system comprising at least one probe, at least one sensing electrode, and a stimulation module; positioning said at least one probe at a target location on the anatomy of said patient; preparing for recordation of said patient's responses to stimulation by positioning said at least one sensing electrode on said patient's anatomy; initiating a direct nerve stimulation protocol; adjusting stimulation parameters of said stimulation protocol to determine a threshold motor response; and identifying said nerve fibers and pathways based on said threshold motor response.

Optionally, said stimulation module comprises a first plurality of twelve output connectors and a second plurality of probe ports.

Optionally, said twelve output connectors enable connection to at least one strip or grid electrode having multiple contacts not exceeding said twelve output connectors.

Optionally, said plurality of probe ports comprises a first probe port and a second probe port and enables connection to said at least one probe, wherein said at least one probe comprises passive and smart probes, and wherein said passive probes include monopolar and bipolar probes.

Optionally, each of the twelve output connectors are configurable as either an anode or a cathode allowing user-defined stimuli to be delivered to arbitrary anode and cathode pairs.

Optionally, said second plurality of probe ports further comprises a third probe port, said third probe port configured for connecting a smart probe and comprising a pair of outputs for connection of an anode and a cathode of said smart probe and a first connection port for power and a second connection port for communications.

Optionally, said at least one sensing electrode includes an EMG needle electrode.

Optionally, said direct nerve stimulation protocol comprises single pulse stimulation, wherein each stimulation has a frequency of 2 to 3 Hz, a pulse width of 200 μsec, an inter-stimulus interval of 1 millisecond and a pulse amplitude of 0.01 mA to 20 mA, with 2 mA or less for cranial nerves and 5 mA or less for peripheral nerves.

The aforementioned and other embodiments of the present shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings:

FIG. 4A illustrates a strip electrode configured in a monopolar setup, in accordance with an embodiment of the present specification;

FIG. 4B illustrates the strip electrode of FIG. 4A configured in a bipolar setup, in accordance with an embodiment of the present specification;

DETAILED DESCRIPTION

Figure 1A:
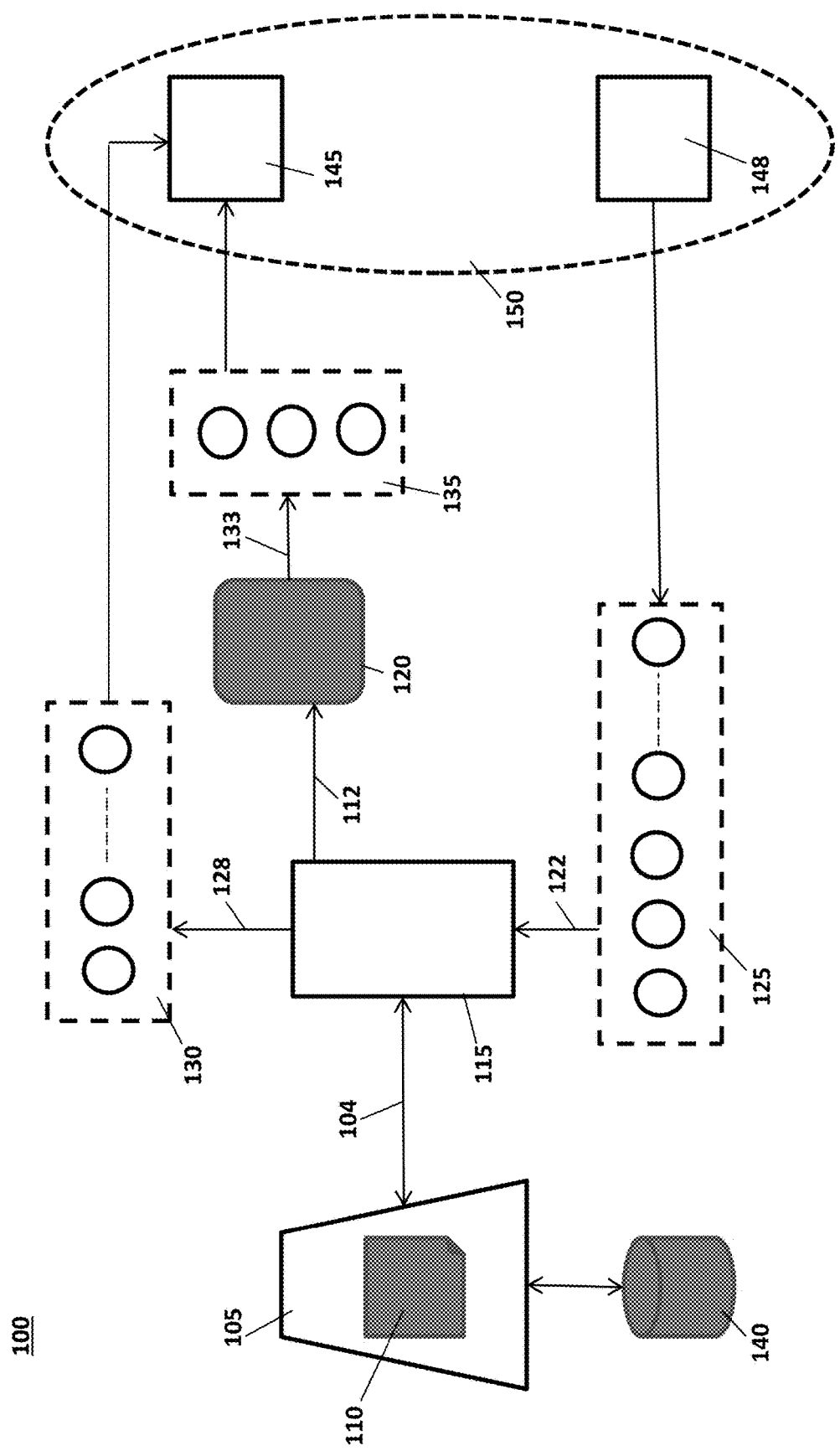
FIG. 1A is a block diagram illustration of an Intraoperative Neuro-Monitoring (IONM) system, in accordance with an embodiment of the present specification.

A "computing device" is at least one of a cellular phone, PDA, smart phone, tablet computing device, patient monitor, custom kiosk, or other computing device capable of executing programmatic instructions. It should further be appreciated that each device and monitoring system may have wireless and wired receivers and transmitters capable of sending and transmitting data. Each "computing device" may be coupled to at least one display, which displays information about the patient parameters and the functioning of the system, by means of a GUI. The GUI also presents various menus that allow users to configure settings according to their requirements. The system further comprises at least one processor (not shown) to control the operation of the entire system and its components. It should further be appreciated that the at least one processor is capable of processing programmatic instructions, has a memory capable of storing programmatic instructions, and employs software comprised of a plurality of programmatic instructions for performing the processes described herein. In one embodiment, the at least one processor is a computing device capable of receiving, executing, and transmitting a plurality of programmatic instructions stored on a volatile or non-volatile computer readable medium. In addition, the software comprised of a plurality of programmatic instructions for performing the processes described herein may be implemented by a computer processor capable of processing programmatic instructions and a memory capable of storing programmatic instructions.

The term 'user' is used interchangeably to refer to a surgeon, neuro-physician, neuro-surgeon, neuro-physiologist, technician or operator of the IONM system and/or other patient-care personnel or staff.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

An Intraoperative Neuro-Monitoring (IONM) System

FIG. 1A is a block diagram illustration of an IONM system 100, in accordance with an embodiment of the present specification. In embodiments, the system 100 enables stimulation based assessment of nerve proximity, direction, pathways and/or changes to nerve pathology, health or status during physically invasive procedures. The system 100 comprises a computing device 105 capable of implementing or executing an IONM software application or engine 110, at least one multi-connection console 115 connected to the computing device 105 using a cable 104, a multi-modality stimulation module 120 connected to the console 115 using a cable 112, a plurality of stimulation components 135 such as, but not limited to, a monopolar probe, a bipolar probe, and a strip or grid electrode along with an integrated or discrete reference electrode capable of being coupled to the stimulation module 120 simultaneously or in any combination thereof via respective cables 133, a plurality of recording or sensing electrodes such as, but not limited to, EMG (Electromyography) electrodes 125 connected to the console 115 through respective cables 122 and a plurality of surgical instruments, components and accessories 130 coupled to the console 115 via respective accessory cables 128. In embodiments of the present specification, the multi-modality stimulation module 120 comprises a plurality of connection ports such that more than one stimulation component 135 may be connected to the system 100 at the same time. Specifically, both a monopolar probe and a bipolar probe can be simultaneously attached to the multi-modality stimulation module 120 without having to unplug and re-plug the probes to switch back and forth between the probes.

In various embodiments, the computing device 105 comprises at least one processor, at least one non-transitory memory, one or more input devices (such as, but not limited to, keyboard, mouse, touch-screen, camera and combinations thereof) and one or more output devices (such as, but not limited to, display screens, printers, speakers and combinations thereof) all of which may be stand-alone, integrated into a single unit, partially or completely network-based or cloud-based, and not necessarily located in a single physical location. The computing device 105 is in data communication with one or more databases 140 that may be co-located with the computing device 105 or located remotely.

The IONM software application or engine 110 implements a plurality of instructions to: deliver a plurality of stimulation protocols or schedules (stored in the one or more databases 140) through any one, any combination or all of the plurality of stimulation components 135, generate a plurality of graphical user interfaces (GUIs) rendered on one or more display screens (that are coupled to the computing device 105) to display a plurality of EMG activity waveforms sensed by the EMG electrodes 125 and extract a plurality of parameters related thereto and enable user-interaction with the system 100 to perform a plurality of functions such as, but not limited to, selecting and activating/initiating one or more stimulation protocols and modulating one or more stimulation parameters of the protocols. The IONM software application or engine 110 is configured to apply one or more stimulation protocols to one or more nerve structures 145 of a patient 150 through the plurality of stimulation components 135 and acquire and record correspondingly evoked EMG activity through the plurality of EMG electrodes 125 positioned within a plurality of muscle sites or locations 148 of the patient 150.

The systems and methods of the embodiments of the present specification are used for mapping and locating anatomical structures and also for assessing these structures, wherein assessing is defined as determining if these structures are functioning in a manner indicative of an underlying disease or, alternatively, are functioning in a non-pathological manner. The functions include, but are not limited to, cognitive functions such as speech and language and motor functions (movement). A neural structure is determined to be functioning based on the presence or absence of a non-pathological response when stimulated. In some embodiments, for a motor response, a non-pathological response is defined as movement or non-movement of a muscle group. In some embodiments, for a cognitive response, a non-pathological response is defined as a patient properly reading a sentence aloud correctly naming a pictured object. It should be appreciated by those of ordinary skill in the art that, although described herein with reference to cortical stimulation and direct nerve stimulation during cerebrospinal surgical procedures, the system 100 and related methods or use cases of the present specification have application in a plurality of surgical procedures during which tissue having critical neural structures must be approached, retracted, and/or impinged upon and consequently requiring that such physically invasive procedures be planned and executed while preserving critical neural structures or bundles. It should also be appreciated that, although embodiments have been described herein with reference to EMG activity, the system 100 and related methods or use cases of the present specification may, in various alternate embodiments, use a plurality of different types of neural monitoring modalities such as, for example, triggered electromyography, spontaneous electromyography, mechanomyography, somatosensory evoked potential, motor evoked potentials, nerve conduction velocity and/or train of fours.

The Multi-Modality Stimulation Module

Figure 1B:
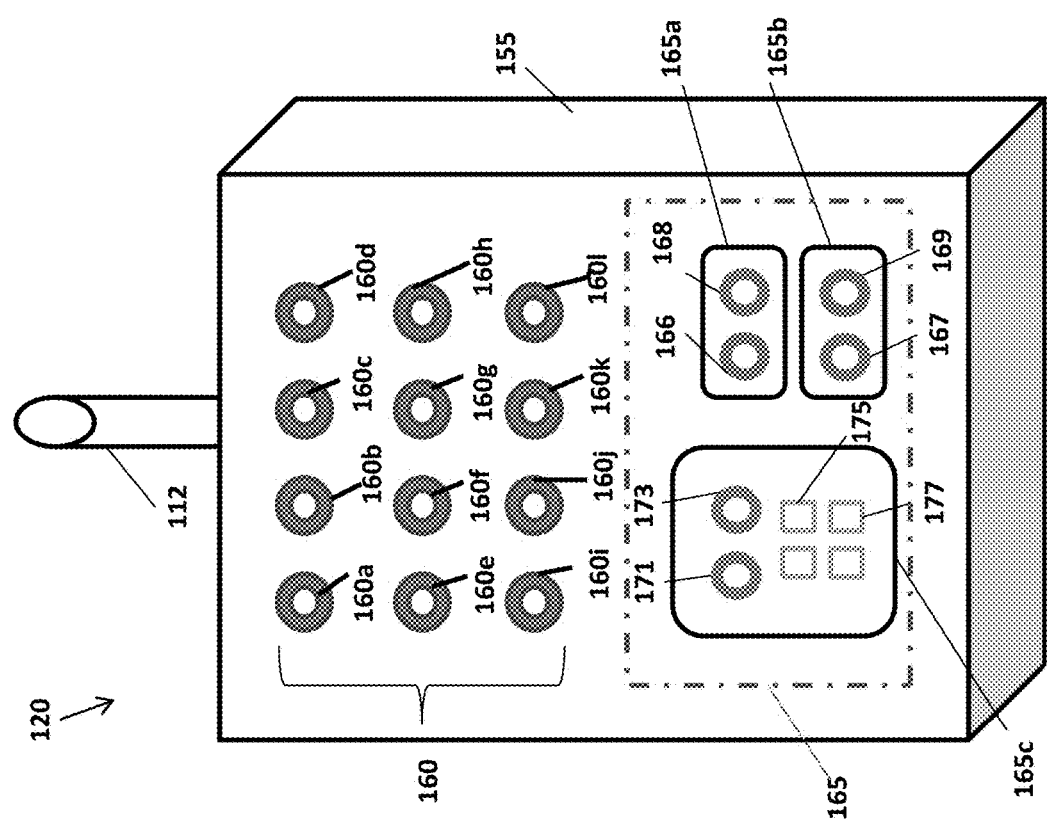
FIG. 1B illustrates a multi-modality stimulation module, in accordance with an embodiment of the present specification.

FIG. 1B illustrates a multi-modality stimulation module 120, in accordance with an embodiment of the present specification. Referring to FIGS. 1A and 1B, the module 120 comprises a housing or enclosure 155 connected, in some embodiments, to a distal end of the electrical cable 112 while a proximal end of the cable 112 is connected to the console 115. In alternate embodiments, the proximal end of the cable 112 may be connected directly to the computing device 105 via a connector such as a D-subminiature connector. In other alternate embodiments, the module 120 may be connected to the console 115 through the electrical cable 112 that serves only to deliver power to the module 120, while the module 120 is in wireless data communication with the computing device 105. Also, in some embodiments, the module 120 is configured as a hand-held device.

In embodiments, the module 120 comprises a first plurality of connectors 160 and a second plurality of separate probe ports 165 (that is, ports 165a, 165b and 165c). In accordance with an embodiment, the first plurality of connectors 160 comprises twelve anode/cathode ports or connectors (160a, 160b, 160c, 160d, 160e, 160f, 160g, 160h, 160i, 160j, 160k, 160l) while the second plurality of separate probe ports 165 comprises a first probe port 165a, a second probe port 165b, and a third probe port 165c. In embodiments, the first probe port 165a and the second probe port 165b are used to connect either a monopolar probe or a bipolar probe and the third probe port 165c is used to connect a smart probe. The first probe port 165a comprises a first output 166 and a second output 168 for connection of an anode and a cathode of a first probe. The second probe port 165b comprises a third output 167 and a fourth output 169 for connection of an anode and a cathode of a second probe. The third probe port 165c comprises a fifth output 171 and a sixth output 173 for connection of an anode and a cathode of a smart probe and a first pair of connection port 175 for power and a second pair of connection port 177 for communications for the smart probe.

The first probe port 165a and the second probe port 165b are both configured to receive either a monopolar probe or a bipolar probe. Therefore, the first probe port 165a and the second probe port 165b allow both a monopolar probe and a bipolar probe to be simultaneously attached to the multi-modality stimulation module 120. A user may perform a procedure on a patient without having to unplug and re-plug monopolar and bipolar probes to switch back and forth between the probes. In various embodiments, the system 100 includes a switching circuit configured to switch each of the twelve ports or connectors 160a-l and each of the outputs 166, 167, 168, 169, 171, 173 such that each connector or output can function as either a cathode output or an anode output.

In embodiments, the twelve ports 160a-160l enable connection to one or more strips, each of which has multiple contacts, not exceeding the twelve ports or channels. In accordance with an embodiment, any of the twelve ports 160a-160l can be configured and flexibly chosen as either an anode or a cathode, thereby allowing user-defined stimuli to be delivered to arbitrary anode and cathode pairs. In one embodiment, a strip or grid electrode, which includes a reference electrode as part of the collection of electrodes contained therein, is connected to the required number of output ports from the available twelve ports 160a-160l.

In embodiments, the second plurality of separate probe ports 165 (that is, ports 165a, 165b and 165c) enables connection to passive and smart probes. In various embodiments, the passive stimulation probes are monopolar and bipolar probes. The smart probe dynamically switches between stimulation functions and provides visual and/or auditory feedback to the user about one or more characteristics (such as, but not limited to, amplitude, latency, location of response, similarity to prior and/or baseline response) of a sensed/detected response. The smart probe (that is available in either a monopolar or a bipolar version) enables the user to control stimulation parameters whereas the passive monopolar and bipolar probes require dependency on another user to adjust parameters using the IONM software engine 110.

Figure 1C:
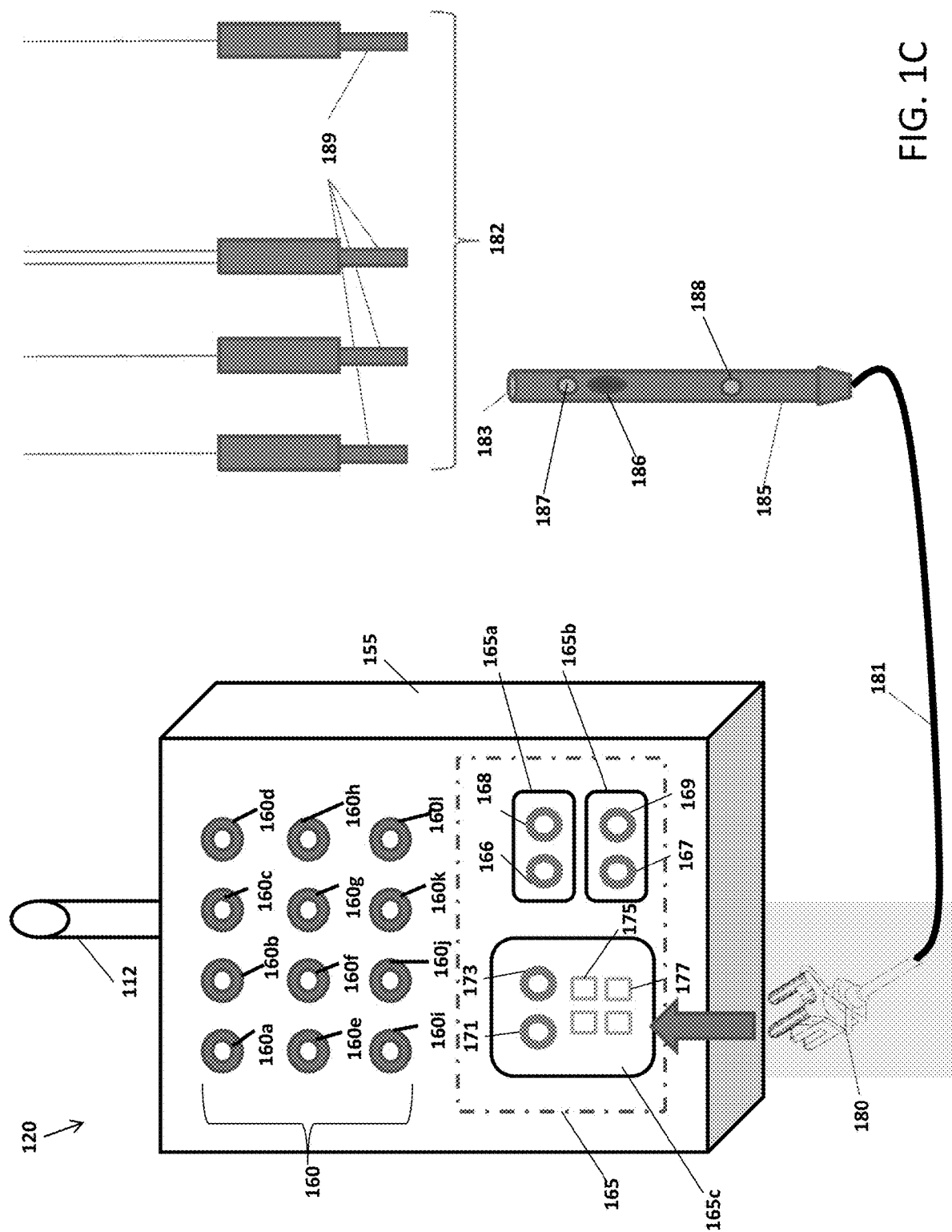
FIG. 1C illustrates a handle in communication with the multi-modality stimulation module of FIG. 1B through an electrical connector, in accordance with an embodiment of the present specification.

In some embodiments, as shown in FIG. 1C, an electrical connector 180 is configured to engage (and disengage) with the third probe port 165c comprising the outputs 171, 173 and the connection port pairs 175, 177. A proximal end of a handle 185 is connected to the connector 180 through a cable 181. A distal end of the handle 185 is configured to (detachably) receive, hold or support a plurality of types (monopolar and bipolar) and sub-types of probe tips 182 such as, for example, a monopolar probe, a monopolar ball tip probe, a bipolar probe, a monopolar/bipolar concentric probe, a monopolar/microfork probe or a monopolar/bipolar prong probe. In embodiments, the probe tips 182 have a common base or connector 189 configured to connect to the handle 185 via a receiving port 183 of the handle. Thus, a plurality of different probe tips can be used with the single handle 185 that is connected to the multi-modality stimulation module 120 via the connector 180. In some embodiments, a design of the electrical connector 180 is of the design disclosed in the assignee's application Ser. No. 29/378,861, now U.S. Pat. No. D670,656, which is hereby incorporated by reference. In embodiments, the handle 185 and probe tip 182 comprise a 'smart probe' and are configured to connect to the module 120 via the connector 180, cable 181, and third probe port 165c.

In some embodiments, the handle 185 has an actuator 186, such as a toggle button, to enable manual switching between monopolar and bipolar modes depending upon the type or subtype of probe tip attached to the handle 185 or a sensing switch configured to enable an automatic switching between modes depending upon the type or subtype of probe tip attached to the handle 185. In some embodiments, the handle 185 also has a visual (light) indicator 187 that indicates monopolar or bipolar modes depending upon the type of probe tip 182 attached to the handle 185, an active or inactive connection state or status of the probe tip 182 attached to the handle 185 and/or which part (monopolar or bipolar) of the prong probe type is active when a monopolar/bipolar prong probe is attached to the handle 185. In some embodiments, the handle 185 further has a visual (light) proximity indicator 188 to provide visual feedback indicative of whether a nerve is far or near from a site where stimulation is being applied. It should be appreciated that the indicator 188 eliminates the need for the user to repeatedly look at a display screen of the IONM system 100. In some embodiments, the proximity indicator 188 is configured to generate or provide at least two indications—a first visual indication (such as, for example, green) signifying that a high stimulation intensity (that is, a stimulation intensity above a predefined threshold stimulation intensity) is required to elicit an evoked response thereby meaning that the site of stimulation is 'far' from the nerve, and a second visual indication (such as, for example, red) signifying that a relatively low stimulation intensity (that is, a stimulation intensity below a predefined threshold stimulation intensity) is required to elicit an evoked response thereby meaning that the site of stimulation is 'near' or 'close' to the nerve.

In embodiments, the power port pair 175 provides power to the handle 185 and probe tip 182 through the connector 180 and cable 181. In embodiments, the communication port pair 177 enables the proximity indicator 188, recordation of the type of stimulator being used and a type of mode (i.e. monopolar and/or bipolar) in clinical data of the IONM system 100, and connection state (i.e. connected or disconnected) of the handle 185 and probe tip 182 type, via the connector 180 and cable 181. The communication port pair 177 may be in data communication with a transceiver to enable the transfer of data.

Figure 2:
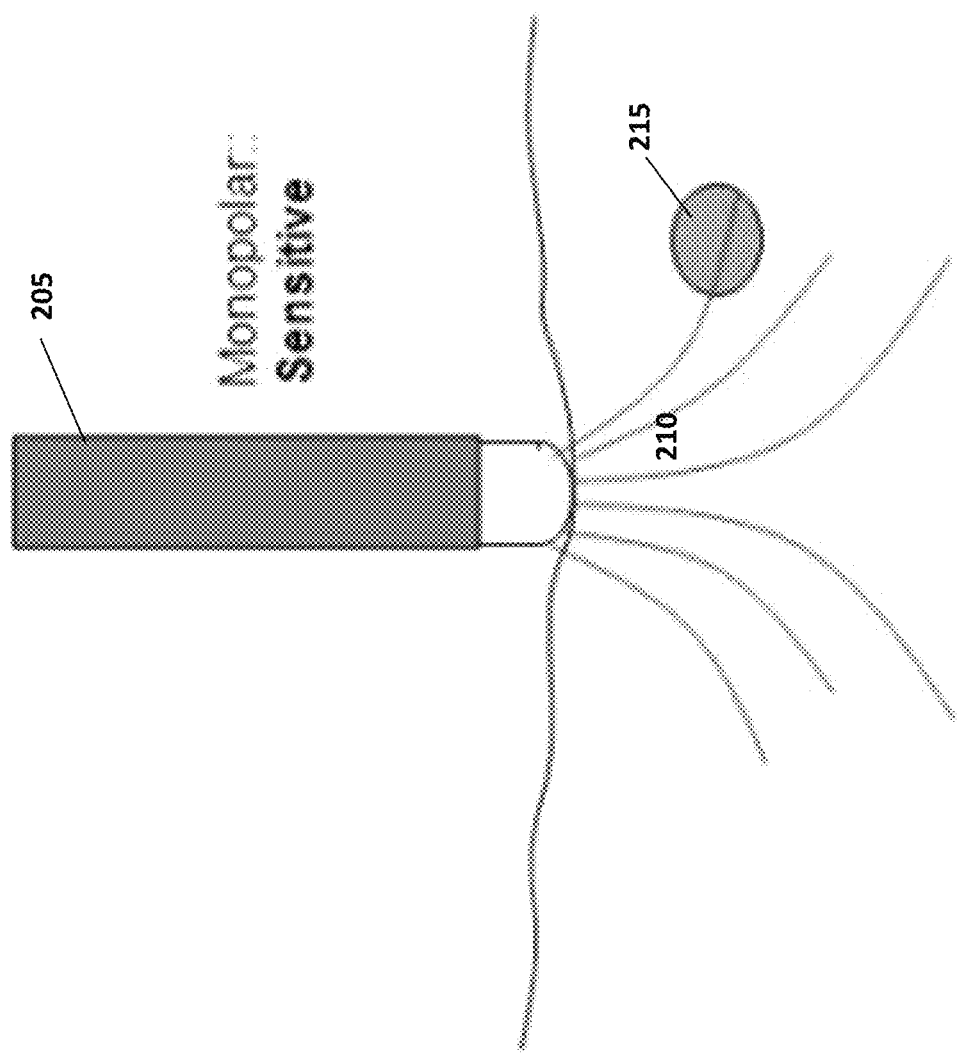
FIG. 2 illustrates a monopolar probe, in accordance with an embodiment of the present specification.
Figure 3:
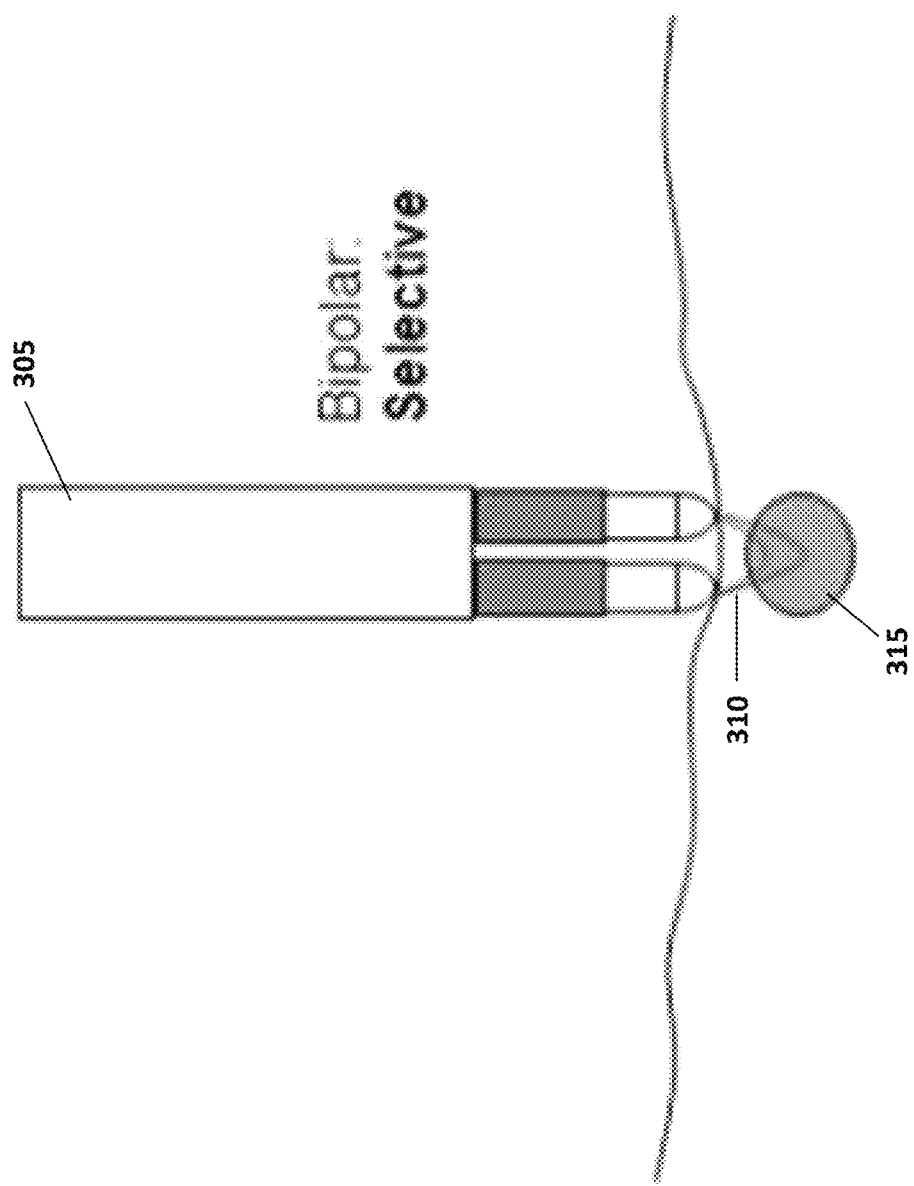
FIG. 3 illustrates a bipolar probe, in accordance with an embodiment of the present specification.

Referring back to FIG. 1A, in accordance with an aspect of the present specification, the stimulation module 120 is configured as a low current stimulator that supports any one or any combination of up to three stimulation modalities—such as, but not limited to, strip or grid electrode, monopolar probe and/or bipolar probe. It should be appreciated that there may be scenarios where one or a combination of the three stimulation modalities may be of value in a surgical procedure, depending on a stage of a surgical procedure and/or based on what anatomical structure is being stimulated. For example, as shown in FIG. 2, a monopolar probe 205 is desirable when sensitivity of a physiological response from the nervous system (such as a muscle action potential) is of priority. The monopolar probe 205 has a spread or expanded field 210 of stimulation to ensure a stimulus encompasses a nerve structure 215. A discrete reference electrode is typically placed some distance away from where the monopolar stimulation probe 205 makes contact. As shown in FIG. 3, a bipolar probe 305 is desirable when selectivity of the stimulus is to be prioritized. The bipolar probe 305 has a focused field 310 of stimulation to apply stimuli to a selective nerve structure 315. However, a strip electrode may perform similarly to a monopolar or bipolar probe in terms of prioritization of sensitivity or selectivity, depending on which contacts of the strip electrode are activated.

FIGS. 4A and 4B illustrate a strip electrode 405 comprising four electrical contacts 410a-410d, in accordance with an embodiment. In FIG. 4A, the strip electrode 405 is configured in a monopolar setup where two contacts 410a and 410d, that are away from each other, are activated. This setup results in stimulation of two neurological structures 415, 416 simultaneously. On the other hand, in FIG. 4B, the strip electrode 405 is configured in a bipolar setup where two contacts 410a and 410b, that are placed closer to each other, are activated. This setup results in stimulation of only one neurological structure 415.

Because an optimal stimulation paradigm may differ across patients and surgical procedure types, the multimodality stimulation module 120 allows the user to easily prepare a varied neuro-stimulation setup, without having to physically move electrodes and/or probes and/or adjust the stimulus paradigm via dials and switches on a device at the computing device or near the OR (operating room) table.

Stimulation Parameters, Protocols or Schedules

The IONM software application of the present specification implements a plurality of stimulation protocols or schedules, comprising a plurality of stimulation parameters, that are available to the user for automatic delivery or application to a patient depending at least upon a combination of the stimulation modalities configured at the stimulation module 120 of FIG. 1B, FIG. 1C, a neurostimulation and neuromonitoring objective such as, but not limited to, cortical stimulation or direct nerve stimulation and/or a surgical procedure being performed. It should be appreciated that the IONM software application provides the user with a degree of independence and automation with respect to delivery of stimuli and recordation of the stimuli as well as that of the correspondingly elicited neuromusculature response.

In various embodiments, stimulation protocols or schedules comprise driving a plurality of stimulation parameters such as, but not limited to, duration of the stimulation; time or moment of application of the stimulation sessions; intensity of stimulations, stimulation pulse shape, frequency, width and amplitude; stimulation duty cycle; stimulation continuity profile. Following are exemplary standard setting ranges for some of the stimulation parameters, including for motor cortex, speech, and language stimulation protocols and a direct nerve stimulation protocol:

Pulse Width: 50 μsec to 2000 μsec and any increment therein

Pulse Amplitude: 0.01 mA to 20 mA and any increment therein

Pulse Frequency: 0.5 Hz to 100 Hz, 100 Hz to 1000 Hz, 100 Hz to 2000 Hz and any increment therein Pulse Shape: Monophasic positive, monophasic negative, biphasic Single Pulse Mode of Stimulation (i.e., direct nerve stimulation protocol) comprising a single pulse stimulation, wherein the single pulse has a frequency in a range of 0.5 to 100 Hz (or any increment therein, preferably 1 to 10 Hz and more preferably 2 to 3 Hz), a pulse width in a range of 1 μsec to 100 milliseconds (preferably 50 to 500 μsec and more preferably 200 μsec), an inter-stimulus interval of 0.5 to 10 milliseconds (or any increment therein, preferably 0.5 to 2 milliseconds, and more preferably 1 millisecond) and a pulse amplitude in a range of 0.01 mA to 20 mA (preferably 1 to 5 mA and more preferably 2 mA or less) for cranial nerves and a pulse amplitude in a range of 0.1 mA to 20 mA (preferably 2 to 8 mA and more preferably 5 mA or less) for peripheral nerves.

Multi-pulse train (MPT) stimulation (i.e. motor cortex stimulation protocol) comprising, for example, 1 to 10 pulses (or any increment therein, preferably 2 to 8 pulses and more preferably 3 to 5 pulses), where each of the pulses is defined by a pulse width in a range of 1 μsec to 100 milliseconds (preferably 250 to 750 μsecs and more preferably 500 μsec), an inter-stimulus interval of 1 to 10 milliseconds (preferably 2 to 4 milliseconds) and a pulse amplitude of 0.01 mA to 100 mA, preferably 0.01 mA to 20 mA.

Duration of stimulation: 5 to 7 seconds

In various embodiments, the IONM software application implements a plurality of sub-sets of the aforementioned stimulation parameters and protocols depending at least upon the type of neurostimulation being delivered—such as, but not limited to, cortical stimulation or direct nerve stimulation.

Use Case Illustrations

In accordance with various aspects of the present specification, the IONM system of the present specification enables the user to apply a plurality of stimulation protocols, patterns or schedules to the patient using at least one or any combination of the three stimulation modalities of the stimulation module with none and/or minimal physical or electromechanical intervention, monitoring and management from the user.

The IONM system of the present specification has application in a plurality of neurostimulation and neuromonitoring scenarios such as, but not limited to, cortical stimulation whereby the motor cortex is stimulated using a strip and/or probe(s) to determine functionality of the cortical structure(s) and direct nerve stimulation whereby a structure is stimulated to determine proximity to nervous system structures and wherein use of one or more types of stimulation probes may be advantageous to create stimulation fields of varying size/depth.

Figure 6:
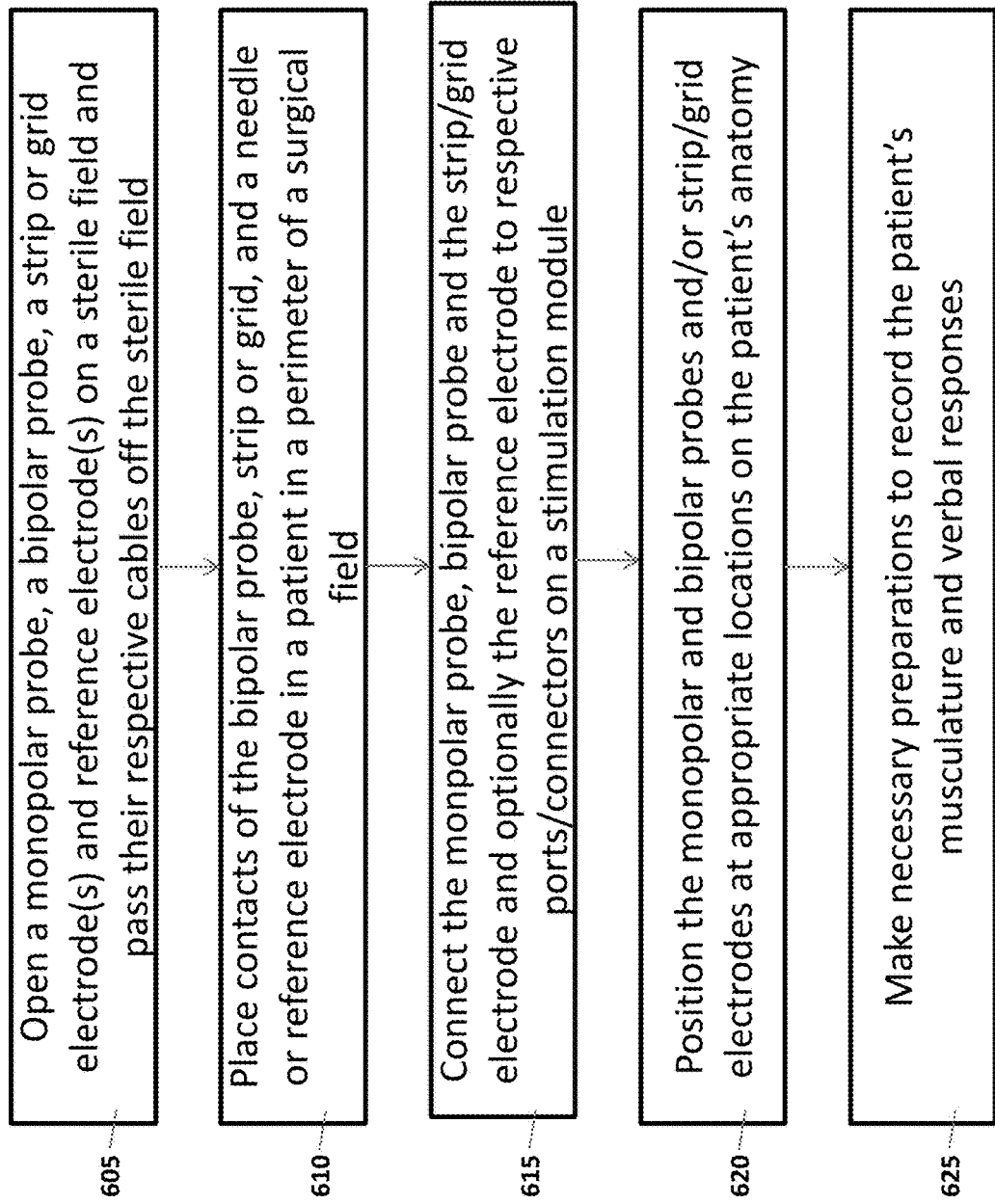
FIG. 6 is a flowchart illustrating a plurality of steps of a use case of cortical stimulation, using the IONM system of the present specification; and, FIG. 7 is a flowchart illustrating a plurality of steps of another use case of direct nerve stimulation, using the IONM system of the present specification.

FIG. 6 is a flowchart illustrating a plurality of steps of a use case of cortical stimulation, using the IONM system of the present specification. Persons of ordinary skill in the art would appreciate that cortical stimulation may be employed in surgical procedures such as, but not limited to, craniotomy for resection of epileptogenic region and for resection of tumor. It should be appreciated that the steps of the use case of FIG. 6 are similar for craniotomy of either resection of epileptogenic region or tumor and that the procedures differ only in the number of strip and/or grid output channels or ports (of the stimulation module 120 of FIG. 1B) used.

Referring now to FIGS. 1B and 6, at step 605 a monopolar probe, a bipolar probe, a strip electrode, and/or grid electrode are opened on a sterile field and their respective connection cables are passed off the sterile field. Optionally, if a monopolar probe is being used, a reference electrode is also opened and its cable is passed off the sterile field. At step 610, contacts of the bipolar probe, monopolar probe, strip electrode and/or grid electrode, and a needle or a reference electrode (for a monopolar probe), are placed in the patient in a perimeter of a surgical field. At step 615, a user connects the monopolar and bipolar probes to the pair of probe ports 165a, 165b and the strip/grid electrode and optionally the reference electrode to the twelve connectors 160a-160l of the stimulation module 120.

Figure 5:
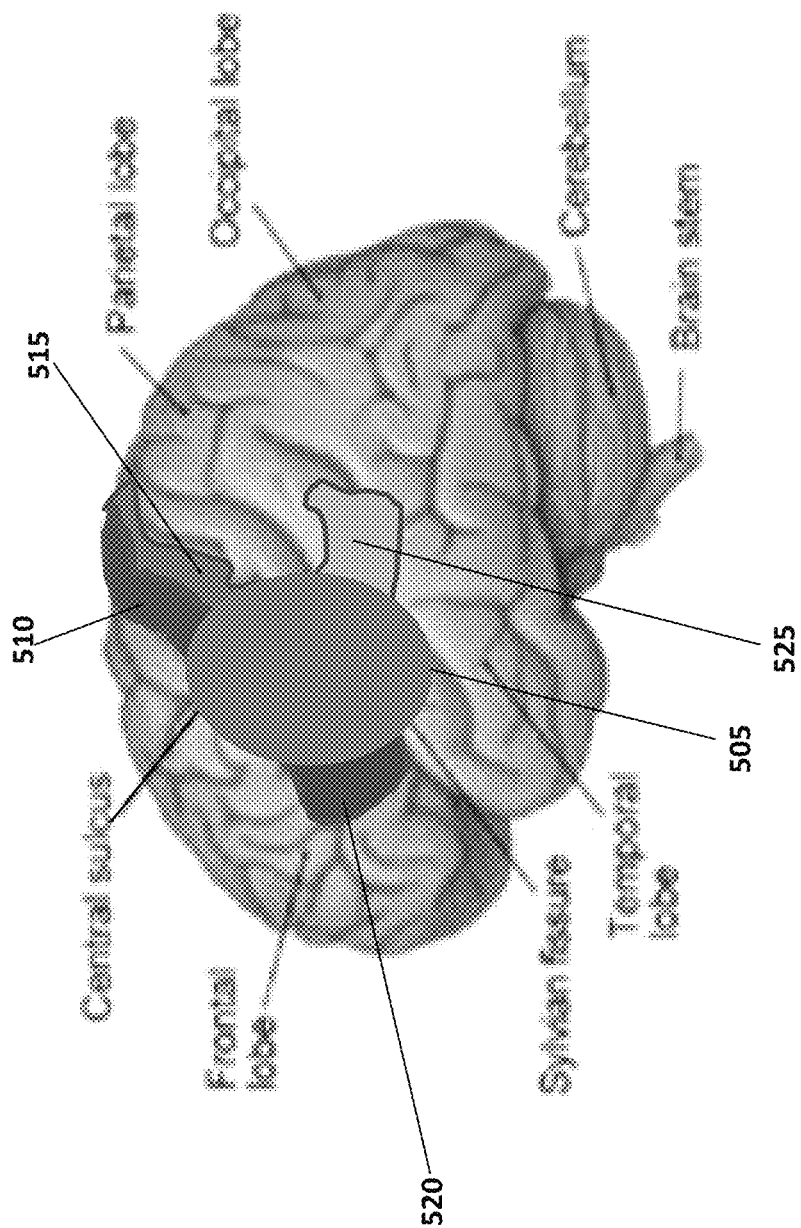
FIG. 5 shows a tumor or epileptogenic region with reference to a map of the functional areas of a human brain, in accordance with an embodiment of the present specification.

At step 620, the monopolar, bipolar probes, strip and/or grid electrodes are positioned at appropriate locations on the patient's anatomy to stimulate, identify, and assess functional areas related to motor, speech and language. In an embodiment, the monopolar probe is used for motor cortex stimulation and the bipolar probe is used for motor cortex and/or speech/language stimulation. FIG. 5 shows a tumor or epileptogenic region with reference to a map of the functional areas of a human brain, in accordance with an embodiment of the present specification. The figure shows the tumor or epileptogenic region 505 encompassing portions of the motor, sensory, speech and language areas 510, 515, 520, and 525. Consequently, resection of the tumor or epileptogenic region 505 poses significant risks to functions associated with the areas 510, 515, 520, and 525. To monitor integrity of neural structures associated with the areas 510, 515, 520, and 525, the monopolar probe is positioned in the motor cortex area 510 while the bipolar probe is sequentially positioned in the motor cortex 510 and/or speech, language areas 520, 525.

Referring back to FIG. 6, at step 625, necessary preparations are made to enable recordation of the patient's musculature responses as a result of motor cortex stimulation and of the patient's verbal responses as a result of stimulation of the speech/language areas.

In some embodiments, a plurality of recording or sensing electrodes are positioned at a plurality of muscle sites of the patient to record responses due to neurostimulation of the patient's motor cortex area. In an embodiment, the recording or sensing electrodes comprise pairs of EMG needle electrodes 125 of FIG. 1A placed in, for example, muscles of the face, arm and leg contralateral to the side of surgery. Recording muscles are chosen based on the location of the tumor or epileptogenic region. Example muscles include orbicularis oculi, orbicularis oris, masseter, mentalis, deltoid, biceps, flexor carpi ulnaris, flexor carpi radialis, abductor digiti minimi, adductor vastus lateralis, tibialis anterior, adductor hallucis. Also, responses to neurostimulation of speech/language areas are documented based on the patient's verbal responses.

At step 630, the user initiates a motor cortex stimulation protocol, using a graphical user interface of the IONM software application. It should be appreciated that the motor cortex stimulation protocol is one of a plurality of stimulation protocols pre-stored in a database associated with the IONM system. In some embodiments, the motor cortex stimulation protocol comprises of the following exemplary parameters and values/ranges:

Mode of Stimulation: Multi-pulse train (for example, 3-5 pulses)
Trigger: Single trigger (that is, single pulse stimulation)
Pulse Width: 500 μsec
Inter-stimulus interval: 2 to 4 milliseconds (equivalent to 250-500 Hz)
Pulse Amplitude: Up to 10 mA (permitted up to 20 mA)

At step 635, the user iteratively adjusts the stimulation parameters, using at least one graphical user interface generated by the IONM software application or engine, to find threshold motor response using monopolar probe, bipolar probe and/or strip/grid electrodes and consequently identify or map functional areas of the motor cortex that need to be preserved during resection. The probes and/or strip/grid electrodes are utilized depending on whether sensitivity or specificity of stimulation is desired.

As an illustration, in one embodiment, the monopolar probe is applied to the patient's motor cortex area for stimulation and the pulse amplitude is modulated in a gradual stepped manner. In some embodiments, the pulse amplitude is modulated automatically by the IONM software engine. For example, the stimulation is initiated with 2 mA and stepped up, say by increments of 2 mA for example, to 10 mA till a muscle response is detected. Suppose that at 10 mA, a 200 μV EMG response is detected at deltoid, biceps, flexor carpi ulnaris. The pulse amplitude is now reduced to 9 mA and a 100 μV EMG response is detected at biceps, flexor carpi ulnaris. The pulse amplitude is now reduced to 8.5 mA that does not produce any EMG response from the muscles. Thus, the pulse amplitude of 9 mA is determined to be the threshold amplitude corresponding to the threshold EMG response. Consequently, the stimulated area is mapped or identified as corresponding to cerebral cortex representing biceps and flexor carpi ulnaris.

Now the bipolar probe is applied to the patient's motor cortex area for stimulation at the first threshold amplitude of 9 mA. However, in an embodiment, a stimulation at 9 mA using the bipolar probe may elicit a response only at the biceps. Consequently, the iterative stimulation process of determining the threshold amplitude and response (as done, earlier, using the monopolar probe) is repeated for the monopolar and bipolar probes at another site on the motor cortex. Let us assume that, at the other site, the threshold amplitude is determined to be 10 mA for orbicularis oculi and orbicularis oris using the monopolar probe and orbicularis oculi only using the bipolar probe.

Next, a strip electrode, such as the electrode 405 of FIGS. 4A, 4B with four contacts 410a-410d, and a reference electrode are placed over the motor cortex area identified as corresponding to orbicularis oculi, orbicularis oris, biceps and flexor carpi ulnaris (as already identified through the earlier performed iterative stimulation processes of determining the threshold amplitude and response). The IONM software now activates different combinations of the four contacts 410a-410d and a reference electrode to stimulate the identified motor cortex area to elicit corresponding motor response. For example, when contacts 410a, 410b are activated there may be no response, when contacts 410a, 410c are activated there may be a response from the orbicularis oculi only, when contact 410b and the reference electrode are activated there may be a response from the orbicularis oris only, when contact 410c and the reference electrode are activated there may be a response from the biceps only. However, when contacts 410b, 410d are activated there may be a response from all muscles. Accordingly, the combination of contacts 410b, 410d is determined to be ideal for frequent stimulation of the motor cortex during resection of the epileptogenic region or tumor.

At step 640, resection of portions of the epileptogenic region or tumor is planned and performed with intent to preserve the neural structures identified and associated with the identified contacts 410b, 410d which elicit response from all muscles. During resection, the monopolar probe is used to stimulate corticospinal tracts (CST) subcortically. An iterative stimulation process, such as one described above using the monopolar probe is used to estimate distance from CST. After completion of the monopolar probe stimulation, stimulation through the four contact strip electrode commences during the resection.

At step 645, the user initiates a speech/language stimulation protocol, using a graphical user interface of the IONM software application. It should be appreciated that the speech/language stimulation protocol is one of a plurality of stimulation protocols pre-stored in the database associated with the IONM system. In some embodiments, the speech/language stimulation protocol comprises of the following exemplary parameters and values/ranges:
Mode of Stimulation: Repetitive train stimulation
Duration of stimulation: 5 to 7 seconds
Pulse Width: 200 μsec
Inter-stimulus interval: 16.6 milliseconds (equivalent to 60 Hz)
Pulse Amplitude: 5 mA (for speech/language responses, which are lower because a patient is awake)

At step 650, the bipolar probe is used to stimulate and map or identify the patient's speech/language areas. The patient is administered with speech/language tasks and the patient's verbal responses are documented while stimulation is delivered to tissues of the speech/language areas. 0Speech arrest and aphasia are examples of patient responses that are indicative that the stimulated tissue corresponds to speech/language functionality.

At step 655, resection of additional portions of the epileptogenic region or tumor is planned and performed with intent to preserve the identified eloquent tissue. Speech/language tasks continue to be administered to the patient throughout resection.

Figure 7:
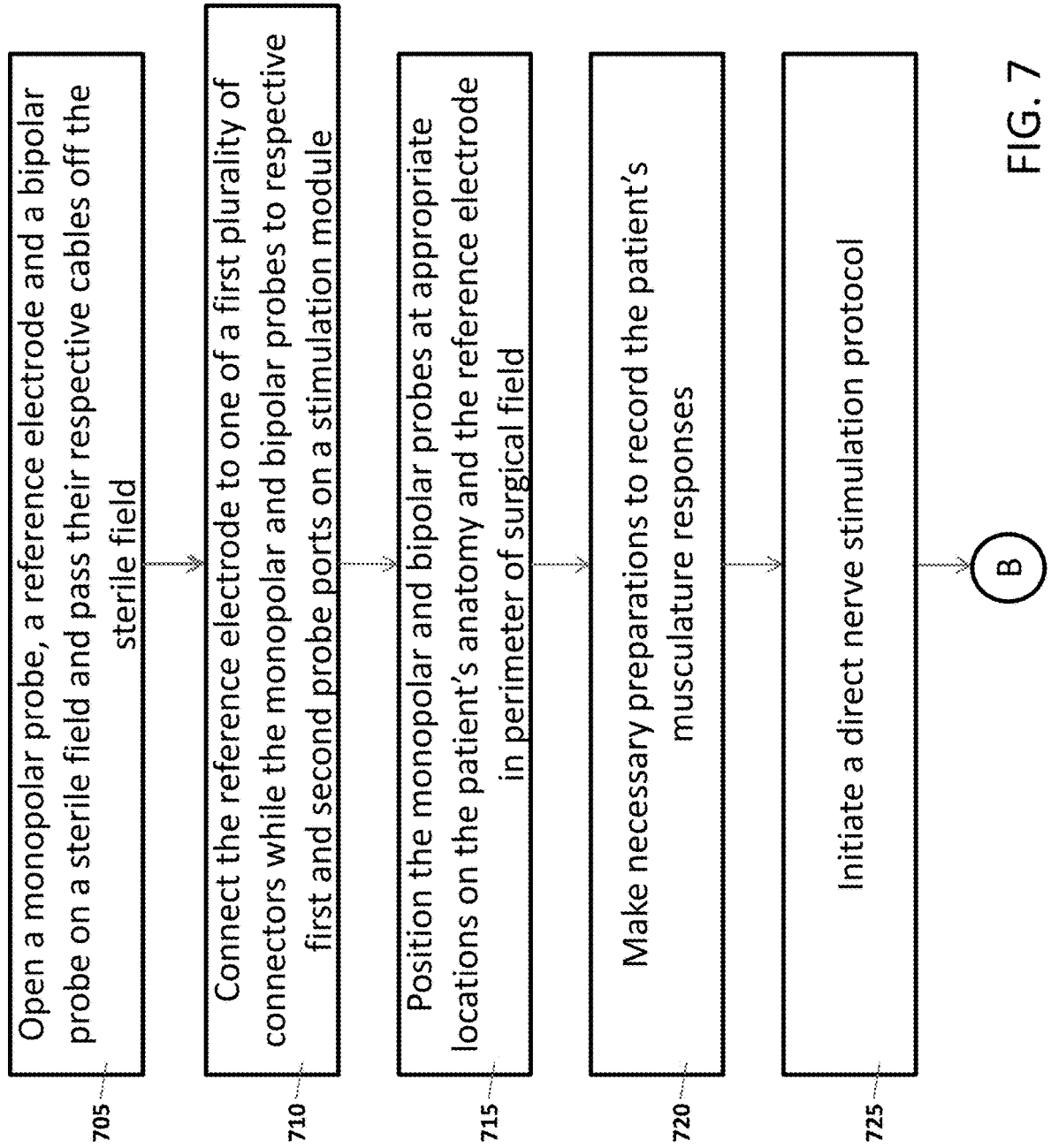

FIG. 7 is a flowchart illustrating a plurality of steps of another use case of direct nerve stimulation, using the IONM system of the present specification. Persons of ordinary skill in the art would appreciate that direct nerve stimulation may be employed in procedures such as, but not limited to, nerve graft, peripheral nerve tumor resection, brachial plexus repair, acoustic neuroma resection and microvascular decompression.

Referring now to FIGS. 1B and 7, at step 705 a monopolar probe, a reference electrode, and a bipolar probe are opened on a sterile field and their respective connection cables are passed off the sterile field. At step 710, a user connects the reference electrode to one of the first plurality of connectors 160 and the monopolar and bipolar probes to the pair of first and second probe ports 165a, 165b of the stimulation module 120.

At step 715, the monopolar and bipolar probes are positioned at appropriate target locations on the patient's anatomy for stimulation and the reference electrode is placed in a perimeter of the surgical field. In an embodiment, the target locations are associated with direct nerve stimulation of peripheral nerves comprising the brachial plexus. At step 720, necessary preparations are made to enable recordation of the patient's musculature responses as a result of direct nerve stimulation of peripheral nerves. In some embodiments, a plurality of recording or sensing electrodes are positioned at a plurality of muscle sites of the patient to record responses due to neurostimulation of the patient's peripheral nerves comprising the brachial plexus. In an embodiment, the recording or sensing electrodes comprise a plurality of pairs of EMG needle electrodes placed in, for example, muscles of the face, arm trunk and/or leg depending on the nerve(s) to be stimulated. Example muscles include trapezius, deltoid, biceps, triceps, flexor carpi ulnaris, flexor carpi radialis, abductor pollicis brevis, and abductor digiti minimi.

At step 725, the user initiates a direct nerve stimulation protocol, using a graphical user interface of the IONM software application. It should be appreciated that the direct nerve stimulation protocol is one of a plurality of stimulation protocols pre-stored in a database associated with the IONM system. In some embodiments, the direct nerve stimulation protocol comprises of the following exemplary parameters and values/ranges:
Mode of Stimulation: Single pulse stimulation
Frequency: 2 to 3 Hz
Pulse Width: 200 μsec
Inter-stimulus interval: 1 millisecond
Pulse Amplitude: Up to 2 mA for cranial nerves and 5 mA for peripheral nerves At step 730, the user iteratively adjusts the stimulation parameters to find threshold response using monopolar probe and/or bipolar probe and consequently map or identify target nerve fibers and pathways that need to be preserved during resection or repair procedures. The probes are utilized depending on whether sensitivity or specificity of stimulation is desired.

As an illustration, in one embodiment, the monopolar probe is applied to the patient's target nerve bundle for stimulation and the pulse amplitude is modulated in a gradual stepped manner. In some embodiments, the pulse amplitude is modulated automatically by the IONM software engine. For example, the stimulation is initiated with 0.5 mA and stepped up, say by increments of 0.5 mA for example, to 2.5 mA till a muscle response is detected. Suppose that at 2.5 mA, a 200 μV EMG response is detected at deltoid, biceps, and triceps. The pulse amplitude is now reduced to 2.2 mA and a 100 μV EMG response is detected at biceps and triceps. The pulse amplitude is now further reduced to 2.1 mA that does not produce any EMG response from the muscles. Thus, the pulse amplitude of 2.2 mA is determined to be the threshold amplitude corresponding to the threshold EMG response of the nerve or nerve fibers that innervate the biceps and triceps. Consequently, the stimulated nerve or nerve fibers are mapped or identified as corresponding to cerebral cortex representing biceps and triceps.

Now the bipolar probe is applied to the patient's target nerve bundle for stimulation at the threshold amplitude of 2.2 mA. However, in an embodiment, the stimulation at 2.2 mA using the bipolar probe may elicit a response only at the biceps. Thus, the pulse amplitude of 2.2 mA is determined to be the threshold amplitude corresponding to the threshold EMG response of the nerve or nerve fibers that innervate the biceps. Consequently, the stimulated nerve or nerve fibers are mapped or identified as corresponding to cerebral cortex representing biceps.

Stimulation of the target nerve bundles is iteratively repeated at different sites of the patient's anatomy and musculature responses are recorded in order to map or identify nerve fibers and pathways that are critical to various motor functions and, therefore, need to be preserved.

At step 735, a procedure comprising tumor resection, nerve repair and/or decompression is planned and performed with intent to preserve the identified nerve fibers and pathways.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A method of using cortical stimulation to assess neural structures during a surgical procedure, the method comprising:
providing an intraoperative neurophysiological monitoring (IONM) system comprising at least one probe, at least one reference electrode, at least one strip electrode or grid electrode, at least one sensing electrode, a stimulation module and a handle having a proximal end configured to connect to the stimulation module and a distal end configured to attach to the at least one probe, wherein the handle comprises a first visual indicator, a second visual indicator, and an actuator configured to automatically switch the stimulation module between a first mode of operation and a second mode of operation depending upon a type of the at least one probe, and wherein the first mode of operation is a bipolar mode and the second mode of operation is a monopolar mode;
placing the at least one reference electrode in a perimeter of a surgical field of a patient;
positioning the at least one probe and/or the at least one strip electrode or grid electrode at target locations on the anatomy of said patient;
preparing for recordation of said patient's responses to stimulation by positioning said at least one sensing electrode on said patient's anatomy;
initiating a stimulation protocol in accordance with the automatically selected first mode of operation or second mode of operation;
adjusting stimulation parameters of the stimulation protocol to determine a threshold response; and
assessing the neural structures based on said threshold response, wherein assessing comprises determining whether the patient's anatomy is functioning in a manner indicative of an underlying disease.

2. The method of claim 1, wherein the stimulation protocol is a motor cortex stimulation protocol, a speech stimulation protocol, or a language stimulation protocol.

3. The method of claim 1, wherein said stimulation module comprises a first plurality of output connectors and a second plurality of probe ports.

4. The method of claim 3, wherein the first plurality of output connectors are configured to enable connection to the at least one strip electrode or grid electrode, wherein the at least one strip electrode or grid electrode has a plurality of contacts and wherein a total number of the plurality of contacts does not exceed a total number of the first plurality of output connectors.

5. The method of claim 3, wherein the second plurality of probe ports comprises a first probe port and a second probe port, wherein each of the first probe port and the second probe port is configured to connect to the at least one probe, wherein the at least one probe comprises passive probes, and wherein the passive probes comprise at least one of a monopolar probe or a bipolar probe.

6. The method of claim 3, wherein each of the plurality of output connectors are configurable as either an anode or a cathode through a user interface in data communication with the IONM system.

7. The method of claim 3, further comprising providing a user interface in data communication with the IONM system, receiving, via the user interface, user-defined stimuli, and delivering signals representative of the user-defined stimuli to pairs of the plurality of output connectors, each of the plurality of output connectors being configurable as either an anode or a cathode through the user interface.

8. The method of claim 3, wherein the second plurality of probe ports comprises a probe port adapted to connect the at least one probe, wherein the at least one probe comprises an anode and a cathode and wherein the probe port comprises first and second outputs for connection of to the anode and the cathode of the at least one probe, a first pair of connection ports adapted to connect to a power supply and a second pair of connection ports adapted to connect to a communication module.

9. The method of claim 1, wherein the at least one sensing electrode comprises an electromyography needle electrode.

10. The method of claim 1, wherein the stimulation protocol comprises a multi-pulse train having 2 to 10 pulses and wherein each of the pulses is defined by a pulse width in a range of 50 μsec to 1000 μsec, an inter-stimulus interval in a range of 0.5 to 10 milliseconds and a pulse amplitude in a range of 0.01 mA to 20 mA.

11. The method of claim 1, wherein the first visual indicator is configured to indicate at least one of the first mode of operation, the second mode of operation, a connection state of the at least one probe or what part of the at least one probe is active.

12. The method of claim 11, wherein the second visual indicator provides a first indication signifying that a site of stimulation is at a first distance from a nerve and a second indication signifying that the site of stimulation is at a second distance from the nerve, wherein the first distance is less than the second distance.

13. A method of using direct nerve stimulation to identify nerve fibers and nerve pathways during a surgical procedure, the method comprising:
providing an intraoperative neurophysiological monitoring (IONM) system comprising at least one probe, at least one sensing electrode, a stimulation module, and a handle having a proximal end configured to connect to the stimulation module and a distal end configured to attach to the at least one probe, wherein the stimulation module comprises at least twelve output connectors and a plurality of probe ports, wherein the handle comprises a first visual indicator, a second visual indicator, and an actuator configured to automatically switch the stimulation module between a first mode of operation and a second mode of operation depending upon a type of the at least one probe, and wherein the first mode of operation is a bipolar mode and the second mode of operation is a monopolar mode;
positioning the at least one probe at a first target location on the patient;
positioning the at least one sensing electrode at a second target location in the patient;
initiating a direct nerve stimulation protocol in accordance with the automatically selected first mode of operation or second mode of operation;

adjusting stimulation parameters of the direct nerve stimulation protocol to determine a threshold motor response; and identifying the nerve fibers and nerve pathways based on the threshold motor response.

14. The method of claim 13, wherein the IONM system further comprises at least one strip electrode or grid electrode having a total number of contacts not exceeding a total number of the at least twelve output connectors, wherein the at least twelve output connectors are adapted to connect to the at least one strip electrode or grid electrode.

15. The method of claim 13, wherein the plurality of probe ports comprises a first probe port and a second probe port and is configured to connect to the at least one probe, wherein the at least one probe comprises at least one passive monopolar probe or passive bipolar probe.

16. The method of claim 13, wherein each of the at least twelve output connectors are configurable as either an anode or a cathode.

17. The method of claim 13, further comprising providing a user interface in data communication with the IONM system, receiving, via the user interface, user-defined stimuli, and delivering signals representative of the user-defined stimuli to pairs of the plurality of output connectors, each of the plurality of output connectors being configurable as either an anode or a cathode through the user interface.

18. The method of claim 13, wherein the plurality of probe ports comprises a probe port configured to connect to the at least one probe, wherein the at least one probe comprises an anode connection and a cathode connection, and wherein the probe port comprises first and second outputs adapted to connect to the anode and the cathode of the probe port, a first pair of connection ports adapted to connect to a power supply and a second pair of connection ports adapted to connect to a transceiver.

19. The method of claim 13, wherein the at least one sensing electrode comprises an electromyography needle electrode.

20. The method of claim 13, wherein the direct nerve stimulation protocol comprises a single pulse stimulation, wherein the single pulse has a frequency of 0.05 Hz to 90 Hz, a pulse width of 50 μsec to 1000 μsec, an interval between pulses of 0.5 millisecond to 10 milliseconds and a pulse amplitude in a range of 0.01 mA to 20 mA.

21. The method of claim 20, wherein the interval between pulses is 2 mA or less for cranial nerves and 5 mA or less for peripheral nerves.

22. The method of claim 13, wherein the first visual indicator is configured to indicate at least one of the first mode of operation, the second mode of operation, a connection state of the at least one probe or what part of the at least one probe is active.

23. The method of claim 22, wherein the second visual indicator provides a first indication signifying that a site of stimulation is at a first distance from a nerve and a second indication signifying that the site of stimulation is at a second distance from the nerve, wherein the first distance is less than the second distance.

* * * * *